US009492596B2

(12) United States Patent
Herweck et al.

(10) Patent No.: US 9,492,596 B2
(45) Date of Patent: Nov. 15, 2016

(54) BARRIER LAYER WITH UNDERLYING MEDICAL DEVICE AND ONE OR MORE REINFORCING SUPPORT STRUCTURES

(75) Inventors: Steve A. Herweck, Nashua, NH (US); Joseph Ferraro, Londonderry, NH (US); Paul Martakos, Pelham, NH (US); Theodore Karwoski, Hollis, NH (US); Anthony Richard Horton, Manchester, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 525 days.

(21) Appl. No.: 11/701,799

(22) Filed: Feb. 2, 2007

(65) Prior Publication Data
US 2008/0109017 A1 May 8, 2008

Related U.S. Application Data

(60) Provisional application No. 60/856,983, filed on Nov. 6, 2006.

(51) Int. Cl.
*A61F 2/02* (2006.01)
*A61L 31/14* (2006.01)
*A61L 31/16* (2006.01)

(52) U.S. Cl.
CPC .............. *A61L 31/145* (2013.01); *A61L 31/16* (2013.01); *A61L 2300/41* (2013.01); *A61L 2300/606* (2013.01)

(58) Field of Classification Search
CPC ................ A61L 31/145; A61L 21/61; A61L 2300/606; A61L 2300/41
See application file for complete search history.

(56) References Cited

U.S. PATENT DOCUMENTS

| | | | |
|---|---|---|---|
| 1,948,959 A | 2/1934 | Croce | |
| 2,368,306 A | 1/1945 | Kiefer et al. | |
| 2,403,458 A | 7/1946 | Ransom | |
| 2,735,814 A | 2/1956 | Hodson et al. | |
| 2,986,540 A | 5/1961 | Posnansky | |
| 3,464,413 A | 9/1969 | Goldfarb | |
| 3,556,294 A | 1/1971 | Walck et al. | |
| 3,567,820 A | 3/1971 | Sperti | |
| 3,803,109 A | 4/1974 | Nemoto et al. | |
| 3,967,728 A | 7/1976 | Gordon et al. | |
| 4,308,120 A | 12/1981 | Pennewiss et al. | |
| 4,323,547 A | 4/1982 | Knust et al. | |
| 4,447,418 A | 5/1984 | Maddoux | |
| 4,557,925 A | 12/1985 | Lindahl et al. | |
| 4,664,114 A | 5/1987 | Ghodsian | |
| 4,813,210 A | 3/1989 | Masuda et al. | |
| 4,814,329 A | 3/1989 | Harsanyi et al. | |
| 4,847,301 A | 7/1989 | Murray | |
| 4,880,455 A | 11/1989 | Blank | |
| 4,883,667 A | 11/1989 | Eckenhoff | |
| 4,886,787 A | 12/1989 | De Belder et al. | |
| 4,894,231 A | 1/1990 | Moreau et al. | |
| 4,895,724 A | 1/1990 | Cardinal et al. | |
| 4,911,707 A | 3/1990 | Heiber et al. | |
| 4,937,254 A | 6/1990 | Sheffield et al. | |
| 4,938,763 A | 7/1990 | Dunn et al. | |
| 4,941,308 A | 7/1990 | Grabenkort et al. | |
| 4,947,840 A | 8/1990 | Yannas et al. | |
| 4,952,419 A | 8/1990 | De Leon | |
| 4,968,302 A | 11/1990 | Schluter et al. | |
| 5,017,229 A | 5/1991 | Burns et al. | |
| 5,061,281 A | 10/1991 | Mares et al. | |
| 5,132,115 A | 7/1992 | Wolter et al. | |
| 5,147,374 A | 9/1992 | Fernandez | |
| 5,151,272 A | 9/1992 | Engstrom et al. | |
| 5,171,148 A | 12/1992 | Wasserman et al. | |
| 5,176,956 A | 1/1993 | Jevne et al. | |
| 5,179,174 A | 1/1993 | Elton | |
| 5,202,310 A | 4/1993 | Levy et al. | |

(Continued)

FOREIGN PATENT DOCUMENTS

| EP | 0 471 566 | 2/1992 |
|---|---|---|
| EP | 0610731 | 8/1994 |

(Continued)

OTHER PUBLICATIONS

Timar-Balzsy et al. (Chemical Principles of Textile Conservation. Oxford: Elsevier Science Ltd., 1998. 117-119).*
Gutfinger, Journal of the American Oil Chemists Society, 58, 11, 1981.*
Sano, New England Journal of Medicine, 336, 1997.*
de la Portilla, Diseases of the Colon and Rectum, 47, 2005.*
Autosuture, "Parietex™ Composite OS Series Mesh," retrieved online at http://www.autosuture.com/AutoSuture/pagebuilder.aspx?topicID=135734&breadcrumbs=135 601:0 (2007).
Rutkow, Ira M. et al., "'Tension-free' inguinal herniorrhaphy: A preliminary report on the 'mesh plug' technique," *Surgery*, vol. 114:3-8 (1993).

(Continued)

*Primary Examiner* — Susan Tran
*Assistant Examiner* — William Craigo
(74) *Attorney, Agent, or Firm* — Wesley Scott Ashton

(57) ABSTRACT

A barrier layer device is formed of an underlying biocompatible structure having a barrier layer coating that can exhibit anti-inflammatory properties, non-inflammatory properties, and/or adhesion-limiting properties, as well as generate a modulated healing effect on injured tissue. As implemented herein, the barrier layer is a non-polymeric cross-linked gel derived at least in part from a fatty acid compound, and may include a therapeutic agent. The underlying structure can be in the form of a surgical mesh. The barrier device is further provided with anchoring reinforcements to aid with the fastening of the barrier device for implantation purposes and reinforcing truss sections or portions that prohibit or substantially reduce the occurrence of excessive stretching and tearing. The barrier device is implantable in a patient for short term or long term applications, and can include controlled release of the therapeutic agent.

24 Claims, 15 Drawing Sheets

(56) References Cited

U.S. PATENT DOCUMENTS

| | | |
|---|---|---|
| 5,254,105 A | 10/1993 | Haaga |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,411,951 A | 5/1995 | Mitchell |
| 5,411,988 A | 5/1995 | Bochow et al. |
| 5,447,940 A | 9/1995 | Harvey et al. |
| 5,464,650 A | 11/1995 | Berg et al. |
| 5,480,653 A | 1/1996 | Aguadisch et al. |
| 5,509,899 A | 4/1996 | Fan et al. |
| 5,547,677 A | 8/1996 | Wright |
| 5,549,901 A | 8/1996 | Wright |
| 5,579,149 A | 11/1996 | Moret et al. |
| 5,580,923 A | 12/1996 | Yeung et al. |
| 5,589,508 A | 12/1996 | Schlotzer et al. |
| 5,591,230 A | 1/1997 | Horn et al. |
| 5,593,441 A | 1/1997 | Lichtenstein et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,629,021 A | 5/1997 | Wright |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,731,346 A | 3/1998 | Egberg et al. |
| 5,736,152 A | 4/1998 | Dunn et al. |
| 5,747,533 A | 5/1998 | Egberg et al. |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A | 1/2000 | Exsted et al. |
| 6,015,844 A | 1/2000 | Harvey et al. |
| 6,028,164 A | 2/2000 | Loomis |
| 6,040,330 A | 3/2000 | Hausheer et al. |
| 6,048,725 A | 4/2000 | Shimada et al. |
| 6,056,970 A | 5/2000 | Greenawalt et al. |
| 6,077,698 A | 6/2000 | Swan et al. |
| 6,080,442 A | 6/2000 | Yoshikawa et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,811 B1 | 6/2001 | Horrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 * | 11/2002 | Abney et al. ................. 554/126 |
| 6,485,752 B1 | 11/2002 | Rein et al. |
| 6,491,938 B2 | 12/2002 | Kunz |
| 6,500,453 B2 | 12/2002 | Brey et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 * | 12/2003 | Pelissier ................... 623/23.74 |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,696,583 B2 | 2/2004 | Koncar et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,323,189 B2 | 1/2008 | Pathak |
| 7,415,811 B2 | 8/2008 | Gottlieb et al. |
| 7,854,958 B2 | 12/2010 | Kramer |
| 7,947,015 B2 | 5/2011 | Herweck et al. |
| 8,124,127 B2 | 2/2012 | Faucher et al. |
| 8,263,102 B2 | 9/2012 | Labrecque et al. |
| 8,308,684 B2 | 11/2012 | Herweck et al. |
| 8,367,099 B2 | 2/2013 | Herweck et al. |
| 8,501,229 B2 | 8/2013 | Faucher et al. |
| 8,722,077 B2 | 5/2014 | Labrecque et al. |
| 9,000,040 B2 | 4/2015 | Faucher et al. |
| 9,012,506 B2 | 4/2015 | Faucher et al. |
| 2001/0025034 A1 | 9/2001 | Arbiser |
| 2001/0025196 A1 | 9/2001 | Chinn et al. |
| 2001/0051595 A1 | 12/2001 | Lyons et al. |
| 2002/0002154 A1 * | 1/2002 | Guivarc'h et al. ........... 514/174 |
| 2002/0007209 A1 | 1/2002 | Scheerder et al. |

(56) References Cited

U.S. PATENT DOCUMENTS

| | | |
|---|---|---|
| 2002/0012741 A1 | 1/2002 | Heinz et al. |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1 | 6/2003 | Chen et al. |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1* | 9/2003 | Ishii et al. ................... 623/1.42 |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0117007 A1 | 6/2004 | Whitbourne et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1* | 10/2004 | Eldridge et al. ............ 606/151 |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0106209 A1 | 5/2005 | Ameri et al. |
| 2005/0112170 A1 | 5/2005 | Hossainy et al. |
| 2005/0113849 A1* | 5/2005 | Popadiuk et al. ............ 606/151 |
| 2005/0124062 A1 | 6/2005 | Subirade |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0051544 A1 | 3/2006 | Goldmann |
| 2006/0058881 A1* | 3/2006 | Trieu ........................ 623/17.16 |
| 2006/0067974 A1 | 3/2006 | Labrecque |
| 2006/0067975 A1* | 3/2006 | Labrecque et al. ........... 424/426 |
| 2006/0067976 A1* | 3/2006 | Ferraro et al. ................ 424/426 |
| 2006/0067977 A1 | 3/2006 | Labrecque et al. |
| 2006/0067983 A1* | 3/2006 | Swanick et al. .............. 424/434 |
| 2006/0068674 A1 | 3/2006 | Dixit et al. |
| 2006/0078586 A1* | 4/2006 | Ferraro et al. ................ 424/423 |
| 2006/0083768 A1* | 4/2006 | Labrecque et al. ........... 424/423 |
| 2006/0088596 A1 | 4/2006 | Labrecque et al. |
| 2006/0093643 A1 | 5/2006 | Stenzel |
| 2006/0110457 A1* | 5/2006 | Labrecque et al. ........... 424/484 |
| 2006/0112536 A1 | 6/2006 | Herweck et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck |
| 2007/0084144 A1 | 4/2007 | Labrecque |
| 2007/0093894 A1 | 4/2007 | Darouiche |
| 2007/0141112 A1 | 6/2007 | Falotico et al. |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck |
| 2008/0118550 A1 | 5/2008 | Martakos et al. |
| 2008/0160307 A1 | 7/2008 | Bauchet |
| 2008/0206305 A1 | 8/2008 | Herweck et al. |
| 2008/0279929 A1 | 11/2008 | Devane et al. |
| 2008/0286440 A1 | 11/2008 | Scheer et al. |
| 2008/0289300 A1 | 11/2008 | Gottlieb et al. |
| 2009/0011116 A1 | 1/2009 | Herweck et al. |
| 2009/0047414 A1 | 2/2009 | Corbeil et al. |
| 2009/0092665 A1 | 4/2009 | Mitra et al. |
| 2009/0181074 A1 | 7/2009 | Makower et al. |
| 2009/0181937 A1 | 7/2009 | Faucher et al. |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2011/0045050 A1 | 2/2011 | Elbayoumi et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |

(56) References Cited

FOREIGN PATENT DOCUMENTS

| | | |
|---|---|---|
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |
| EP | 2083875 | 8/2009 |
| EP | 1 402 906 | 6/2011 |
| KR | 20080025986 | 3/2008 |
| WO | WO 86/00912 | 7/1984 |
| WO | WO 90/01969 | 3/1990 |
| WO | 90/08544 A1 | 8/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | 98/46287 A2 | 10/1998 |
| WO | WO 98/54275 | 12/1998 |
| WO | WO 99/25336 | 5/1999 |
| WO | WO 00/40278 | 7/2000 |
| WO | WO 00/62830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO 02/100455 | 12/2002 |
| WO | WO 03/000308 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO 03/039612 | 5/2003 |
| WO | WO 03/041756 | 5/2003 |
| WO | WO 03/070125 | 8/2003 |
| WO | WO 03/092741 | 11/2003 |
| WO | WO 03/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | 2004101010 A1 | 11/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | 2005/082434 A2 | 9/2005 |
| WO | WO 2005/116118 | 12/2005 |
| WO | PCT/US05/034610 | 3/2006 |
| WO | WO 2006/024488 | 3/2006 |
| WO | PCT/US05/034601 | 4/2006 |
| WO | WO 2006/036967 | 4/2006 |
| WO | PCT/US05/034615 | 5/2006 |
| WO | PCT/US05/034941 | 5/2006 |
| WO | PCT/US05/034681 | 7/2006 |
| WO | PCT/US05/034682 | 7/2006 |
| WO | PCT/US05/034836 | 7/2006 |
| WO | PCT/US05/034614 | 8/2006 |
| WO | WO 2006/102374 | 9/2006 |
| WO | PCT/US06/037184 | 2/2007 |
| WO | PCT/US05/034678 | 3/2007 |
| WO | WO 2007/047028 | 4/2007 |
| WO | PCT/US06/040753 | 9/2007 |
| WO | 2008/010788 A2 | 1/2008 |
| WO | 2008/016664 A2 | 2/2008 |
| WO | WO-2008/057328 A2 | 5/2008 |
| WO | PCT/US06/040753 | 10/2008 |
| WO | PCT/US08/071565 | 11/2008 |
| WO | PCT/US08/071547 | 2/2009 |
| WO | PCT/US08/085386 | 2/2009 |
| WO | PCT/US07/022860 | 4/2009 |
| WO | PCT/US07/022944 | 4/2009 |
| WO | PCT/US07/019978 | 5/2009 |
| WO | PCT/US09/037364 | 8/2009 |
| WO | 2010/042134 A1 | 4/2010 |
| WO | 2010/042241 A1 | 4/2010 |
| WO | PCT/US08/071565 | 4/2010 |
| WO | PCT/US08/071547 | 9/2010 |
| WO | PCT/US10/026521 | 9/2010 |
| WO | PCT/US08/071547 | 10/2010 |
| WO | WO 2012/009707 | 1/2012 |

OTHER PUBLICATIONS

International Search Report for Application No. PCT/US2008/000565, dated May 4, 2009.
Binder et al., "Chromatographic Analysis of Seed Oils. Fatty Acid Composition of Castor Oil," The Journal of the American Oil Chemists' Society, vol. 39:513-517 (1962).
CECW-EE, "Ch. 4: Coating Types and Characteristics," Engineering and Design—Painting: New Construction and Maintenance, pp. 4-1 to 4-24 (1995).
Wikipedia, "Sirolimus," pp. 1-13, available online at http://en.wikipedia.org/wiki/Sirolimus, date accessed May 11, 2011.
U.S. Appl. No. 11/236,908, Mar. 25, 2006, Non-final, US 2006/0067974.
U.S. Appl. No. 11/236,908, Aug. 24, 2009, Final, US 2006/0067974.
U.S. Appl. No. 11/236,943, Dec. 23, 2009, Final, US 2006/0067975.
U.S. Appl. No. 11/236,943, Mar. 5, 2009, Non-final, US 2006/0067975.
U.S. Appl. No. 11/236,977, Aug. 3, 2009, Non-final, US 2006/0088596.
U.S. Appl. No. 11/237,263, Jul. 7, 2010, Final, US 2006/0110457.
U.S. Appl. No. 11/237,263, Oct. 7, 2009, Non-final, US 2006/0110457.
U.S. Appl. No. 11/237,264, Jun. 2, 2010, Final, US 2006/0067983.
U.S. Appl. No. 11/237,264, Oct. 5, 2009, Non-final, US 2006/0067983.
U.S. Appl. No. 11/237,264, Nov. 23, 2010, Final, US-2006-0067983.
U.S. Appl. No. 11/237,420, Mar. 5, 2009, Non-final, US 2006/0078586.
U.S. Appl. No. 11/237,420, Dec. 6, 2010, Non-final, US-2006-0078586.
U.S. Appl. No. 11/237,420, Nov. 4, 2009, Final, US 2006/0078586.
U.S. Appl. No. 11/238,532, Mar. 30, 2009, Non-final, US 2006-0067976.
U.S. Appl. No. 11/238,532, Sep. 9, 2009, Final, US 2006-0067976.
U.S. Appl. No. 11/238,554, May 12, 2010, Final, US 2006/0121081.
U.S. Appl. No. 11/238,554, Oct. 9, 2009, Non-final, US 2006/0121081.
U.S. Appl. No. 11/238,554, May 1, 2009, Final, US 2006/0121081.
U.S. Appl. No. 11/238,554, Jul. 25, 2008, Non-final, US 2006/0121081.
U.S. Appl. No. 11/238,564, Apr. 16, 2008, Non-final, US 2006-0083768.
U.S. Appl. No. 11/238,564, Aug. 6, 2009, Final, US 2006-0083768.
U.S. Appl. No. 11/239,555, Mar. 30, 2009, Non-final, US 2006-0067977.
U.S. Appl. No. 11/525,328, Apr. 30, 2007, Non-final, US 2007/0084144.
U.S. Appl. No. 11/525,390, Jul. 14, 2010, Non-final, US 2007/0071798.
U.S. Appl. No. 11/582,135, Nov. 9, 2010, Non-final, US 2007/0202149.
U.S. Appl. No. 11/582,135, Jan. 6, 2010, Non-final, US 2007/0202149.
U.S. Appl. No. 11/582,135, May 12, 2009, Non-final, US 2007/0202149.
U.S. Appl. No. 11/978,840, Dec. 3, 2010, Non-final, US-2008-0118550.
U.S. Appl. No. 12/075,223, Dec. 8, 2010, Non-final, US-2008-0206305.

(56) References Cited

OTHER PUBLICATIONS

U.S. Appl. No. 12/325,546, Feb. 25, 2010, Non-final, US 2009/0181937.
U.S. Appl. No. 12/325,546, Aug. 31, 2010, Final, US 2009/0181937.
U.S. Appl. No. 12/364,763, Dec. 11, 2009, Non-final, US 2009/0208552.
U.S. Appl. No. 12/364,763, Sep. 21, 2010, Final, US 2009/0208552.
U.S. Appl. No. 11/236,908, May 5, 2009, US 2006/0067974.
U.S. Appl. No. 11/237,420, May 5, 2009, US 2006/0078586.
"Cure" in Academic Press Dictionary of Science and Technology (1992).
"Polymerization" Merriam-Webster Online Dictionary, retrieved from <www.merriam-webster.com> on Dec. 13, 2009; Merriam-Webster's Inc. 2009; pp. 1.
A paper entitled "Evaluation of the Biocompatibility and Drug Delivery Capabilities of Biological Oil Based Stent Coatings" by Shengqio Li of the Katholieke Universiteit Leuven.
Ahuja et al. "Prevention of Postoperative Intraperitoneal Adhesions—An Experimental Study in Rats", Journal of Indian Pediatric Surgery 2002 7:15-20.
Camurus, "In our endeavors to create the unique, we start with the best. Your product.".
De Scheerder, Ivan K. et al. "Biocompatibility of polymer-coated oversized metallic stents implanted in normal porcine coronary arteries," Atherosclerosis, vol. 114:105-114.
Drummond, Calum J. et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Guler et al. (Some empirical equations for oxopolymerization of linseed oil. Progress in Organic Coatings 2004, vol. 51, 365-371).
Hwang, Chao-Wei et al, "Physiological Transport Forces Govern Drug Distribution for Stent-Based Delivery," Circulation, vol. 104:600-605 (2001).
Jonasson, Lena et al., "Cyclosporon A inhibits smooth muscle proliferation in the vascular response to injury," Proc. Natl. Acad. Sci. USA, vol. 85: 2303-2306 (1988).
Mallegol et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).
Ogunniyi, D.S., "Castor oil: A vital industrial raw material," Biosource Technology, vol. 97: 1086-1091 (2006).
Redman, L.V. et al., "The drying rate of raw paint oils—a comparison," The Journal of Industrial and Engineering Chemistry, vol. 5: 630-636 (1913).
Salu, Koen J. et al, "Addition of cytochalasin D to a biocompatible oil stent coating inhibits intimal hyperplasia in a porcine coronary model," Coronary Artery Disease, vol. 14(8):545-555 (2003).
Scheller, Bruno et al, "Addition of Paclitaxel to Contrast Media Prevents Restenosis After Coronary Stent Implantation," Journal of the American College of Cardiology, vol. 42(8):1415-1420 (2003).
Shahidi, Fereidoon ed.; "Bailey's Industrial Oil and Fats Products" 2005; John Wiley and Sons; vol. 5, Edible Oil and Fat Products: Processing Technologies, pp. 1-15.
Van der Giessen, Willem J. et al, "Marked Inflammatory Sequelae to Implantation of Biodegradable and Nonbiodegradable Polymers in Porcine Coronary Arteries," Circulation, vol. 94:1690-1697 (1996).
Websters Dictionary Online, Accessed on Feb. 13, 2009, entry for "polymer" p. 1 of 1.
International Search Report for International Application PCT/US10/052899, dated Jan. 10, 2011.

Final Office Action for U.S. Appl. No. 11/236,908 (listed on SB/08 as US 2006/0067974), mailed May 17, 2011.
Final Office Action for U.S. Appl. No. 11/525,390 (listed on SB/08 as US 2007/0071798), mailed Feb. 21, 2011.
Final Office Action for U.S. Appl. No. 11/582,135 (listed on SB/08 as US 2007/0202149), mailed May 12, 2011.
Non-final Office Action for U.S. Appl. No. 11/980,155 (listed on SB/08 as US 2008/0113001), mailed Mar. 24, 2011.
Interview summary for U.S. Appl. No. 11/236,908 (listed on SB/08 as US 2006/0067974) mailed Dec. 2, 2010.
Interview summary for U.S. Appl. No. 11/582,135 (listed on SB/08 as US 2007/0202149) mailed Dec. 7, 2010.
Interview summary for U.S. Appl. No. 12/325,546 (listed on SB/08 as US 2009/0181937) mailed Dec. 2, 2010.
Interview summary for U.S. Appl. No. 12/364,763 (listed on SB/08 as US 2009/0208552) mailed Dec. 2, 2010.
Crivello et al., "Epoxidized triglycerides as renewable monomers in photoinitiated cationic polymerization," Chem. Mater, 1992:692-699.
Encylopedia Britannica Online, "Surface Coating," available online at http://www.britannica.com/EBchecked/topic/575029/surface-coating>, date accessed Jun. 17, 2011.
Supplementary European Search Report in Application No. EP 05 80 4291, dated Jul. 26, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 85 8430, dated Aug. 18, 2011.
Non-final Office Action for U.S. Appl. No. 11/525,390, mailed Jul. 11, 2011.
Final Office Action for U.S. Appl. No. 11/237,420, mailed Jul. 13, 2011.
Final Office Action for U.S. Appl. No. 12/075,223, mailed Aug. 11, 2011.
Final Office Action for U.S. Appl. No. 11/978,840, mailed Jun. 22, 2011.
Non-Final office Action for U.S. Appl. No. 11/582,135, mailed Oct. 14, 2011.
Final Office Action for U.S. Appl. No. 11/980,155, mailed Oct. 21, 2011.
Non-Final Office Action for U.S. Appl. No. 11/236,908, mailed Dec. 2, 2011.
Ackman, R.G., "Fish Oils", *Bailey's Industrial Oil and Fat Products*, 6th Edition, 279-317 (2005).
Andes, et al. "Antiproliferative Strategies for the Treatment of Vascular Proliferative Disease", *Current Vascular Pharmacology*, 1)1):85-98 2003.
Jorge, N., "Grasas y Aceites", 48(1): 17-24, (1997).
Lipids, Chapter 19, pp. 1-12 (2002).
Winter, et al., "Physical and Chemical Gelation" *Encyclopedia of Materials—Science and Technology*, vols. 1-11: 6691-6999 (2001).
International Search Report for PCT/US2011/44292, dated Dec. 6, 2011.
Supplementary European Search Report for Application No. EP 12004057, dated Apr. 10, 2013.
Supplementary European Search Report for Application No. EP 08877338.7, dated Aug. 16, 2012.
Supplementary European Search Report for Application No. EP09819594.4, dated Aug. 14, 2012.
Notice of Allowance for U.S. Appl. No. 12/182,261 (listed on SB/08 as US US-2009-0047414), mailed Jul. 23, 2012.
Advisory Action for U.S. Appl. No. 12/401,243 (listed on SB-08 as US 2010-0233232), mailed Aug. 27, 2012.
Final Office Action for U.S. Appl. No. 12/581,582 (listed on SB-08 as US 2010/0183697) mailed Aug. 29, 2012.
Notice of Allowance for U.S. Appl. No. 11/525,390 (listed on SB/08 as US-2007/0071798), mailed Oct. 4, 2012.
Advisory Action for U.S. Appl. No. 12/581,582 (listed on SB-08 as U.S. Publication No. 2010-0183697), dated Nov. 14, 2012.
Notice of Allowance for U.S. Appl. No. 11/525,390 (listed on SB-08 as U.S. Publication No. US-2007-0071798), dated Nov. 20, 2012.

(56) References Cited

OTHER PUBLICATIONS

Notice of Allowance for U.S. Appl. No. 11/525,390 (listed on SB/08 as US-2007/0071798), mailed Nov. 30, 2012.
Non-Final Office Action for U.S. Appl. No. 13/404,487 (listed on SB-08 as US 2012-0213839), dated Dec. 20, 2012.
Non-Final Office Action for U.S. Appl. No. 13/184,512 (listed on SB-08 as 2012-0016038), dated Jan. 31, 2013.
Non-Final Office Action for U.S. Appl. No. 11/978,840 (listed on SB-08 as U.S. No. US-2008-0118550), dated Feb. 19, 2013.
Non-Final Office Action for U.S. Appl. No. 13/682,991 (listed on SB-08 as U.S. Publication No. US-2013-0074452), dated Mar. 18, 2013.
Notice of Allowance for U.S. Appl. No. 13/404,487 (listed on SB-08 as U.S. Publication No. US-2012-0213839), dated Apr. 2, 2013.
Non-Final Office Action for U.S. Appl. No. 11/236,943 (listed on SB-08 as U.S. Publication No. US-2006-0067975), dated Apr. 22, 2013.
Final Office Action for U.S. Appl. No. 13/184,512 (listed on SB-08 as U.S. Publication No. U.S. 2012-0016038), date Jun. 25, 2013.
Non-Final Office Action for U.S. Appl. No. 13/593,656 (listed on SB-08 as U.S. Publication No. US-2012-03115219), dated Jul. 15, 2013.
Notice of Allowance for U.S. Appl. No. 13/682,991 (listed on SB-08 as U.S. Publication No. US 2013-0074452), dated Aug. 1, 2013.
Notice of Allowance for U.S. Appl. No. 11/978,840 (listed on SB-08 as U.S. Publication No. US-2008-0118550), dated Aug. 6, 2013.
Mallegol, "Long-Term Behavior of Oil-Based Varnishes and Paints Photo-and Thermooxidation of Cured Linseed Oil", *Journal of the American Oil Chemists' Society*, 77:257-263 (2000).
International Search Report for International Application PCT/US2013/044653, dated Sep. 4, 2013.
Non-Final Office Action for U.S. Appl. No. 11/237,420 (listed on SB-08 as U.S. Publication No. US-2006-0078586), dated Nov. 12, 2013.
Non-Final Office Action for U.S. Appl. No. 12/075,223 (listed on SB-08 as U.S. Publication No. US-2008-0206305), dated Nov. 12, 2013.
Non-Final Office Action for U.S. Appl. No. 11/980,155 (listed on SB-08 as U.S. Publication No. US-2008-0113001), dated Nov. 12, 2013.
Final Office Action for U.S. Appl. No. 12/182,261 (listed on SB-08 as US 2009/0047414) mailed Apr. 30, 2012.
Final Office Action for U.S. Appl. No. 12/401,243 (listed on SB-08 as US 2010/0233232) mailed Jun. 11, 2012.
Final Office Action for U.S. Appl. No. 12/185,165 (listed on SB-08 as US 2009/0011116) mailed Apr. 6, 2012.
Non-Final Office Action for U.S. Appl. No. 12/182,261 (listed on SB/08 as US 2009/0047414), mailed Dec. 21, 2011.
Non-Final Office Action for U.S. Appl. No. 12/401,243 (listed on SB/08 as US 2010/0233232) mailed Jan. 5, 2012.
Non-Final Office Action for U.S. Appl. No. 12/182,165 (listed on SB/08 as US 2009/0011116), mailed Jan. 5, 2012.
Non-Final Office Action for U.S. Appl. No. 12/581,582 (listed on SB-08 as US 2010/0183697) mailed Mar. 14, 2012.
Notice of Allowance for U.S. Appl. No. 11/236,908 (listed on SB/08 as US 2006/0067974) mailed May 11, 2012.
Notice of Allowance for U.S. Appl. No. 11/582,135 (listed on SB/08 as US 2007/0202149), mailed Jan. 9, 2012.
Supplementary European Search Report for Application No. EP 10825447, dated Mar. 31, 2014.
Non Final Office Action for U.S. Appl. No. 12/325,546 (listed on SB-08 as U.S. Publication No. US-2009-0181937), dated Apr. 22, 2014.
Non Final Office Action for U.S. Appl. No. 12/364,763 (listed on SB-08 as U.S. Publication No. US-2009-0208552), dated Apr. 23, 2014.
Non Final Office Action for U.S. Appl. No. 12/401,243 (listed on SB/08 as US 2010- 0233232), mailed May 8, 2014.
Notice of Allowance for U.S. Appl. No. 11/237,264 (listed on SB-08 as U.S. Publication No. US-2006-0067983), dated Mar. 27, 2014.

Notice of Allowance for U.S. Appl. No. 11/237,263 (listed on SB-08 as U.S. Publication No. US-2006-0110457), dated Mar. 27, 2014.
Final Office Action for U.S. Appl. No. 11/236,943 (listed on SB-08 as U.S. Publication No. US-2006-0067975), dated Dec. 4, 2013.
Final Office Action for U.S. Appl. No. 11/237,264 (listed on SB-08 as U.S. Publication No. US-2006-0067983), dated Dec. 17, 2013.
Notice of Allowance for U.S. Appl. No. 13/593,656 (listed on SB-08 as U.S. Publication 2012-03115219), dated Jan. 24, 2014.
Non-Final Office Action for U.S. Appl. No. 13/843,068, dated Sep. 29, 2014.
Notice of Allowance for U.S. Appl. No. 11/236,943 (listed on Sb-08 as U.S. Publication No. US-2006-0067975), dated Oct. 6, 2014.
Non-Final Office Action for U.S. Appl. No. 13/184,512, dated Oct. 10, 2014.
Non-Final Office Action for U.S. Appl. No. 12/075,223, dated Oct. 29, 2014.
Uchida, et al., "Swelling Process and Order-Disorder Transition of Hydrogel Containing Hydrophobic Ionizable Groups", *Macromolecules*, 28, 4583-4586 (1995).
Non Final Office Action for U.S. Appl. No. 12/581,582 (listed on SB-08 as U.S. Publication 2010-0183697), dated May 29, 2014.
Non-Final Office Action for U.S. Appl. No. 13/943,489, dated Jul. 1, 2014.
Final Office Action for U.S. Appl. No. 11/980,155, dated Jul. 21, 2014.
Final Office Action for U.S. Appl. No. 11/237,420, dated Jul. 22, 2014.
Final Office Action for U.S. Appl. No. 12/581,582, dated Jan. 8, 2015.
Final Office Action for U.S. Appl. No. 12/401,243, dated Jan. 16, 2015.
Non-Final Office Action for U.S. Appl. No. 11/237,420, dated Jan. 21, 2015.
Notice of Allowance for U.S. Appl. No. 13/943,489, mailed Jan. 29, 2015.
Non-Final Office Action for U.S. Appl. No. 11/980,155, dated Nov. 7, 2014.
Notice of Allowance for U.S. Appl. No. 12/364,763 (listed on SB-08 as U.S. Publications No. US-2009-0208552), dated Dec. 5, 2014.
Notice of Allowance for U.S. Appl. No. 12/325,546 (listed on SB-08 as U.S. Publication No. US-2009-0181937), dated Dec. 8, 2014.
Final Office Action for U.S. Appl. No. 13/843,068, dated Apr. 23, 2015.
Final Office Action for U.S. Appl. No. 13/184,512, dated Apr. 28, 2015.
H. Fineberg et al., Industrial Use of Fish Oils, pp. 222-238, http://spo.nmfs.noaa.gov/Circulars/CIRC278.pdf, downloaded Aug. 3, 2015.
Lewis, Richard J., Sr., Hawley's Condensed Chemical Dictionary, 2001, pp. 308, 309 and 896-898, 14th edision, John Wiley & Sons, Inc., New York.
Webster's II New College Dictionary (1995), 1075, Houghton Mifflin Company, New York, US.
Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
SepraFilm Adhesion Barrier package insert (Genzyme Biosurgery 2008).
Sannino, Alessandro, et al., Biodegradeable Cellulose-based Hydrogels: Design and Applications, 2 Materials, pp. 353-373, 2009.
Heinz, Thomas, Carboxymethyl Ethers of Cellulose and Starch—A Review, Center of Excellence for Polysaccharide Research, Friedrich Schiller University of Jena (Germany), pp. 13-29, 2005.
Omidian, H. et al., Swelling Agents and Devices in Oral Drug Delivery, J. Drug. Del. Sci. Tech., No. 18, vol. 2, 2008, pp. 83-93.
Kamel, S. et al., Pharmaceutical Significance of Cellulose: A Review, Express Polymer Letters vol. 2, No. 11, 2008, pp. 758-778.

(56) References Cited

OTHER PUBLICATIONS

Adel, A. M. et al., Carboxymethylated Cellulose Hydrogel: Sorption Behavior and Characterization, Nature and Science, No. 8, vol. 8, 2010, pp. 244-256.
Bacteria in Water, The USGS Water Science School, http://water.usgs.gov/edu/bacteria.html (downloaded Nov. 9, 2015).
Novotny, L. et al., Fish: a potential source of bacterial pathogens for human beings, VET. MED.—Czech, 49, 2004, vol. 9, pp. 343-358.
Allergies, Asthma and Allergy Foundation of America (2011), http://www.aafa.org/page/types-of-allergies,aspx (downloaded Oct. 5, 2015).
Sicherer, Scott H., Food Allergies: A Complete Guide for Eating When Your Life Depends on it, 2013, 15, Johns Hopkins University Press, Baltimore, MD, USA.
Omega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).
Soy Allergy, Asthma and Allergy Foundation of America (2005), http://www.aafa.org/display.cfm? id=9&sub=20&cont=522 (downloaded Nov. 10, 2015).
Refined soybean oil not an allergen, say food scientists, Food navigator-usa.com (2005), http://www.foodnavigator-usa.com/content/view/print/127438 (downloaded Nov. 10, 2015).
Yanyaee, R. et al., Waste fish oil biodiesel as a source of renewable fuel in Iran, Renewable and Sustainable Energy Reviews, 2013, pp. 312-319, 17, Elsevier Ltd.
Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/hrb-20059372?p=1 (downloaded Sep. 28, 2015).
Milk allergy, at http://www.mayoclinic.org/diseases-conditions/milk-allergy/basics/definition/con-20032147?p=1 (downloaded Jul. 29, 2015).
Soy allergy, at http://www.mayoclinic.org/diseases-conditions/soy-allergy/basics/definition/con-20031370?p=1 (downloaded Jul. 29, 2015).
F.D. Gunstone, Fatty Acid and Lipid Chemistry 72 (1999).
Hawley'S Condensed Chemical Dictionary 315, 316, 332, 333, 334, 825 and 826 (2001).
Hutlin, Herbert O. et al., Chemical Composition and Stability of Fish Oil (International Association of Fish Meal Manufacturers Apr. 10, 1991).
F.V.K Young, The Chemical & Physical Properties of Crude Fish Oils for Refiners and Hydrogenators, 18 Fish Oil Bulletin 1-18 (1986).
Karrick, Neva L., Nutritional Value of Fish Oils as Animal Feed, Circular 281 (Fish and Wildlife Service Bureau of commercial Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel: an In Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).

Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.
Novavax, retrieved online at http://www.novavax.com/go.cfm?do=Page.View&pid=3 (2006).
Orthovisc, "New Treatment Option is Potential Alternative to OTC Pain Medications for Osteoarthritis of the Knee" retrieved online at http://www.jnj.com/innovations/new_features/ORTHOVISC.htm:essionid=33N2RBQDV0DZKCQPCCEGU3AKB2IIWTTI (2006).
Orthovisc, "What is ORTHOVISC®?" retrieved online at http://www.orthovisc.com/xhtmlbgdisplay.jhtml?itemname=about_orthovisc (2005).
Orthovisc, "Your Knees and Osteoarthritis", retrieved online at http://www.orthovisc.com/xhtmlbgdisplay.jhtml?itemname=understanding_knee_oa (2003).
Orthovisc, "What to expect from your treatment," retrieved online at http://www.orthovisc.com/xhtmlbgdisplay.jhtml?itemname=what_to_expect (2007).
Orthovisc, "Tools and Resources for Managing Your Osteoarthritis", retrieved online at http://www.orthovisc.com/xkhtmlbgdisplay.jhtml?itemname=patient_resources (2007).
Pohibinska, A., et al., "Time to reconsider saline as the ideal rinsing solution during abdominal surgery", The American Journal of Surgery, vol. 192, pp. 281-222 (2007).
Singh, Alok, et al., "Facilitated Stent Delivery Using Applied Topical Lubrication", Catherization and Cardiovascular Interventions, vol. 69, pp. 218-222 (2007).
Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (!987).
Hortolam, Juliane G., et al., "Connective tissue diseases following silicone breast implantation: where do we stand?", Clinics, 2013, vol. 3, p. 281.
Lidar, M. et al., "Silicone and sclerodema revisited", Lupus, 2012, vol. 21, pp. 121-127.
"Lead", Article by Centers for Disease Control and Prevention (CDC), Nov. 2009, 2 pages.
Triglycerides, https://www.lipid.org/sites/default/files/triglycerides.pdf (downloaded Sep. 24, 2015).
Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015).
Swanson, Danielle, et al., Omega-3 Fatty Acids EPA and DHA: Health Benefits Throughout Life, 3 Advances in Nutrition 1-7 (American Society for Nutrition 2012).
Fats & Oils (2008) at http://scifun.chem.wisc.edu/chemweek/pdf/fats&oils.pdf (downloaded Sep. 24, 2015).
Wicks et al. Organic Coatings:Science and Technology 1999 New York:Wiley Interscience, pp. 258-267.
Mills et al. Oils and Fats. "The Organic Chemistry of Museum Objects" London:Buttersworth and Co. 1987, pp. 26-40.
Erhardt Paints Based on Drying Oil Media. Painted Wood: History & Conservation. Ed. Berland Singapore: The J. Paul Getty Trust 1998. pp. 17-32.
Wexler et al. Chemical Reviews 1964, vol. 64, No. 6, pp. 591-611.
Polymer—The Chambers 21st Century Dictionary M. Robinson and G. Davidson (Eds.), London, United Kingdom: Chambers Harrap. Retrieved from http://search.credoreference.com/content/entry/chambdict!polymer/O.

(56) References Cited

OTHER PUBLICATIONS

Polymer—Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst!polymer/0.

Falagas et al. European Society of Clinical Microbiology and Infection Diseases, 2005, vol. 11, pp. 3-8.

Bimbo, International Fishmeal & Oil Manufacturers Association, 1998, vol. 9, No. 5, pp. 473-483.

Wikipedia, Sunflower oil, https://en.wikipedia.org/wiki/Sunflower_oil, accessed Jul. 23, 2015 in related U.S. Appl. No. 14/252,671, pp. 1-7.

Esoteric Oils, Peppermint essential oil information, http://www.essentialoils.co.za/essential-oils/peppermint.htm, accessed Jul. 23, 2015 in related U.S. Appl. No. 14/252,671, pp. 1-7.

Orthomolecular, Fish Oil, Jun. 29, 2004, http://orthomolecular.org/nutrients/fishoil.html, accessed Jul. 22, 2015 in related U.S. Appl. No. 14/252,671, p. 1.

\* cited by examiner

BARRIER LAYER WITH UNDERLYING MEDICAL DEVICE AND ONE OR MORE REINFORCING SUPPORT STRUCTURES

RELATED APPLICATION

This application claims priority to U.S. Provisional Application Ser. No. 60/856,983, filed on Nov. 6, 2006. This application also claims the benefit of said Application for all subject matter in common with this application. The disclosure of said Applications is hereby incorporated herein by reference in its entirety.

FIELD OF THE INVENTION

The present invention relates to implantable devices forming tissue separating layers, and more particularly to a soft tissue device having one or more reinforcing support truss structures for reinforcing the implantable devices. The one or more reinforcing support truss structures may be placed in a location to improve the mechanical strength of the device.

BACKGROUND OF THE INVENTION

Biocompatible medical films are most often used in surgical settings as a physical barrier to help separate certain organs from adjacent tissues and medical devices following surgical intervention or blunt dissection to minimize adhesion formation. For example, SEPRAFILM®, a product of Genzyme Corporation of Cambridge, Mass., is used in patients undergoing either open or laparoscopic abdominal or pelvic surgeries as an implantable treatment intended to reduce the incidence, extent, and severity of postoperative adhesion formation between different tissues and organs and implantable medical devices such as soft tissue support membranes and mesh, or combinations of non-absorbable films and meshes.

U.S. Pat. No. 5,017,229 is directed to a water insoluble, biocompatible gel that includes the reaction product of hyaluronic acid, a polyanionic polysaccharide, and an activating agent. The gel described in the '229 patent can be provided in the form of an adhesion prevention composition, such as a membrane or composition suitable for incorporation into a syringe. The gel is described as being able to form a film by being cast into a sheet form, extruded, compressed, or allowed to dehydrate in a flat sheet. When modified with polysaccharide, the biodegradable film forms the above-described SEPRAFILM® adhesion-limiting or adhesion barrier product made commercially available as a dehydrated bio-dissolvable single layer sheet.

However, such commercially available adhesion prevention and adhesion barrier film products often can be difficult to handle and apply to the targeted location due to their chemical make up and rapid bio-dissolvable properties. The composition and limited structural strength properties of these bio-dissolvable products result in the material forming the products softening relatively quickly upon exposure to fluids, thus making handling difficult during most open and laparoscopic surgical intervention operations. Furthermore, many of these bio-dissolvable films are made intentionally to be thin and without reinforcement or anchoring support to minimize tissue disruption and consequently end up being structurally weak (i.e., easily torn or folded during handling). These characteristics of the film products result in a very low level of mechanical fixation integrity and a very low level of handling stability during surgical manipulation and implantation. These characteristics are intentional, principally to enhance rapid body fluid absorption and subsequent chemical breakdown and liquefication by body fluids for complete absorption and removal by the body. Chemically stabilized adhesion prevention film products engineered solely for adhesion prevention or temporary barrier separation are also known to be difficult to handle during surgery because of a tendency for the materials to adhere to themselves, and are known to tear and fold undesirably during handling and implantation.

Surgical meshes, which are used to reinforce weakened areas of abdominal, pelvic, or thoracic tissues, or to replace a portion of internal structural soft tissue that has neither been damaged nor removed surgically, can also be made to have anti-adhesion properties. PCT Application Publication No. WO 2004/028583 is directed to compositions, devices, and methods for maintaining or improving the integrity of body passageways following surgery or injury. Surgical mesh drug eluting delivery devices can include one or more therapeutic agents provided with a drug eluting mesh wrap implant placed adjacent to medical devices and internal tissue as described therein. The meshes are available in various single layer, multi-layer, and 3-dimensional configurations made without bio-absorbable adhesion coatings and films. The meshes are most often constructed of synthetic non-absorbable polymer materials, such as polyethylene, polytetrafluoroethylene, and polypropylene, and can include a carrier having a therapeutic agent attached thereto, incorporated within, or coated thereon. The mesh structure for this surgical application serves as a drug eluting delivery apparatus for local therapeutic delivery within the body. Affixing the carrier and or coating directly onto the surgical mesh makes it easier to handle the device without the drawbacks of film, namely tearing, folding, and rapid dissolving when contacting body fluids, and the lack of fixation or anchoring means. Non-absorbable mesh structures generally provide more handling strength and directional placement control during installation than bio-absorbable or bio-dissolvable polymer films. However, surgical mesh structures are not structurally designed to create barrier layer separation between tissue and medical devices due to their inherent porous structure. Such devices do enable some form of mechanical fixation or anchoring ability not possible with films, but the strength of the mesh structures can be insufficient to adequately hold fixation and anchoring devices without tearing, material disruption, elongation, and/or separation from its anchoring mechanism(s).

For most surgical procedures involving internal tissue reconstruction, dissection, or soft tissue repair, there is often a need to reinforce the surgically effected area with a non-absorbable implantable structure (such as a mesh or porous polymeric film). Such devices require an anchor, suture, adhesive, or tack to hold the mesh (or other device) in place within the patient's body to avoid migration, material separation, folding, wrinkling, or clumping of the implanted device after the surgery is complete.

All known implantable reinforcement devices, including non-absorbable surgical mesh and porous polymer films, are designed to promote either uninhibited cellular in-growth or limited cellular in-growth through the medical device over time. After tissue begins growing into and through the surgically implanted porous mesh or film, the implanted device is further anchored or held in place by that ingrown tissue, in addition to the surgically applied mechanical anchoring means. However, prior to such tissue in-growth, which can take days, weeks, or even months, depending on the condition of the patient and the location of the implant and damaged tissue, it is necessary to hold the mesh, or other device, in place with such fasteners as anchors, sutures, tacks, or adhesives.

These various mechanical fasteners involve either passage directly through an existing hole in the porous implant, or forcibly puncturing the implant, forming a new button hole or other aperture through the device, causing some damage to the material during the anchoring process. Apertures or points of anchoring created in the porous mesh and film devices are subject to increased mechanical stress because the fastener or adhesive applying additional force against the apertures or points of anchoring to hold the implant in place against soft tissue. These increased fixation stresses have, at times, resulted in the device becoming separated from its anchoring mechanism due to excessive material stretching and/or tearing. At the apertures or points of anchoring, the underlying tissue during normal physical activity can sometimes unpredictably pull the anchoring means through the aperture or button hole, leaving this portion of the implanted device un-anchored. Even more problematic for the medical user is, when tensioning the implant to remove folds or wrinkles, an anchored location pulls free, or pulls through the mesh device.

The tearing of the device at or near areas of anchoring mechanisms, depending on the particular fastener used, can allow the implanted device to become disrupted from its preferred location, or to lift up and off the anchoring mechanism, leaving the non-attached portion of the device disconnected from the tissue it was meant to reinforce. The excessive stretching and tearing, either during surgical installation or immediately following surgery during normal physical activity can result in complications derived from the implant becoming un-anchored or disconnected from the tissue, which can be clinically detrimental to the patient. Such detachment events are often referred to as "re-occurrences", and generally require surgical-re-intervention, additional blunt dissection, or separation of adjoining tissues to re-establish a desirable and anatomically suitable fixation spot to re-attach the implant material. In the event the implant anchoring hole has torn or has elongated under stress conditions, often the implant cannot be repaired or re-attached at the location of the tear or stretch, thus requiring removal of the implant and/or introduction of a replacement implant device, requiring additional anchors to new tissue locations to patch over the damage caused by the events related to the first implant.

In addition to providing an inadequate means for anchoring, these implantable devices may become deformed during and/or after implantation. During implantation these reinforced implantable devices may be stretched or distorted. After the reinforced implantable device is implanted, the anatomical area it is intended to cover may have an irregular surface such that the reinforced implantable device may be distorted to conform to the irregular surface. For example, in case where a patient has an abdominal defect, the reinforced implantable device may conform to the defect, which in some cases may be an undesired result. The distorting and stretching that occurs during and/or after implantation may cause temporary or permanent deformations and reduce the effectiveness of the reinforced implantable device. These deformations may become more pronounced as the size of the reinforced implantable devices increases.

SUMMARY

There is a need for a tissue separating layer implantable device, with or without the ability to deliver therapeutic agents, but having a structure predisposed to promoting tissue in-growth on one side and providing adhesion-limiting characteristics on an opposite side, with one or more surfaces that modulate healing, and limit or reduce the degree of adhesion formation with adjacent tissues and/or other medical devices, while also being reinforced to prevent or substantially reduce the occurrence of deformation, such as stretching or distorting, during and/or after implantation. The reinforcing of the device can be achieved using one or more reinforcing support truss structures. Locations and/or the number of reinforcing support truss structures may vary based on the anatomical application.

In addition, one or more anchoring elements may be provided to reinforce locations of anchoring to prevent, or substantially, reduce the occurrence of excessive stretching or tearing at the locations of anchoring. The anchoring of the device to the tissue can occur with adhesive, sutures, staples, tacks, or other anchoring or fastening devices commonly applied for affixing mesh or film directly to tissue. The present invention is directed toward further solutions to address this need, in addition to having other desirable characteristics.

In one aspect, a barrier layer device is disclosed that includes a base surgical mesh structure, at least one anchoring support element, at least one reinforcing support truss structure, and a barrier layer. The base surgical mesh sheet structure is generally flexible and is defined by a perimeter. The at least one anchoring support element is disposed on a surface of the base surgical mesh structure at a location suitable for anchoring the device. The at least one anchoring support element is adapted to reinforce the location suitable for anchoring. The at least one reinforcing support truss structure is disposed on a surface of the at least one base surgical mesh structure and extends between edges of the perimeter and across the surface of the base surgical mesh structure to reinforce the barrier layer device. The barrier layer is formed on at least one of at least a portion of the at least one surgical mesh structure, the at least one anchoring support element, or the at least one reinforcing support truss structure.

In another aspect, a barrier layer device is disclosed that includes a first base surgical mesh structure, a second base surgical mesh structure, at least one anchoring support element, at least one reinforcing support truss structure and a barrier layer. The at least one anchoring support element disposed on a surface of at least one of the first base surgical mesh structure or the second base surgical mesh structure. The at least one reinforcing support truss structure, the first base surgical mesh structure, the second base surgical mesh structure and the at least one anchoring support element form a reinforced structure. The at least one reinforcing support truss structure extends across the surface of at least one of the first base surgical mesh structure or second base surgical mesh structure. The barrier layer is formed on at least one of at least a portion of the first base surgical mesh structure, the second base surgical mesh structure, the at least one anchoring support element, or the at least one reinforcing support truss structure.

In yet another aspect, a method for creating an implantable barrier layer device is disclosed. The method includes obtaining a first mesh, a second mesh, at least one anchor support element and at least one reinforcing support truss structure. The method also includes attaching the first mesh, the second mesh, the at least one anchor support element and the at least one reinforcing support truss structure to form a reinforced underlying structure. The reinforcing support truss structure is attached to the first and second meshes to reinforce a location absent the first and second meshes or a location where the first and second meshes are attached. The method further includes forming a barrier layer on at least a portion of the reinforced underlying structure.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
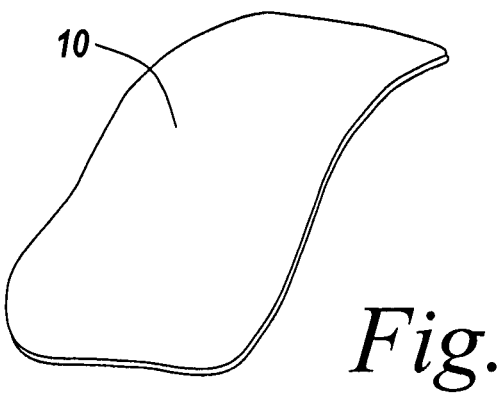
FIG. 1 a diagrammatic illustration of a barrier layer realized as a stand alone film, according to one embodiment of the present invention.

An illustrative embodiment of the present invention relates to the provision of a barrier layer that can exhibit modulated healing properties, anti-inflammatory properties, non-inflammatory properties, and/or adhesion-limiting properties, and corresponding method of making, along with a combined barrier layer and medical device, to form a barrier device. The barrier layer can be combined with another medical device, such as a device having a mesh structure, which can provide underlying internal support to the barrier layer while the barrier layer can provide any of the above mentioned properties to the medical device, in addition to improved healing and delivery of therapeutic agents including, but not limited to analgesic, antiproliferative, antimicrobial, and anti-infective agents.

The barrier layer is generally formed of biocompatible oil, or an oil composition formed in part of a biocompatible oil. In addition, the oil composition can include a therapeutic agent component, such as a drug or other bioactive agent. As implemented herein, the barrier layer is a non-polymeric cross-linked gel derived at least in part from a fatty acid compound. The barrier layer in the present invention is combined with an underlying structure, such as a surgical mesh, to create the inventive barrier device.

The barrier device includes one or more reinforcing support truss structures to provide additional mechanical strength to the barrier device to prevent or reduce the occurrence of distortion or stretching of the barrier device during and/or after implantation.

The term "reinforcing support truss structure" refers to a supportive structure to aid in reducing or eliminating the effects of tension, compression, shearing, bending, etc.; thereby stabilizing the barrier device. The number, size, shape and location of the reinforcing support truss structures can be determined based on the size, shape, desired anatomical application, etc., of the barrier device. In general, a reinforcing support truss structure occupies less area than the underlying barrier device. In this manner, a reinforcing truss structure provides additional supportive strength to the barrier device without compromising the generally flexible nature of the barrier device.

The reinforcing support truss structure can extend between edges of a perimeter of the barrier device and can extend across a surface of a surgical mesh of the barrier device. The one or more reinforcing support truss structures can be selectively located based on an anatomical application. The reinforcing support truss structures may prevent or reduce overall deformation of the barrier device and/or can also prevent or reduce localized deformation of the barrier device. As one example, the barrier device can be implanted in the abdominal region of a patient where the abdominal region has a defect, such as a hole. The barrier device can be positioned such that the reinforcing support truss structure is aligned with the defect so that the barrier device does not conform to the defect. As another example, the barrier device can be positioned on the thoracic region. In this example, the reinforcing support truss structures may be aligned in a position where ribs that were removed for surgery would be located to provide additional mechanical strength to the barrier device and the patient's thoracic cavity when the patient's thoracic cavity expands and contracts. The number and location of reinforcing support truss structures that are included in the barrier device can vary based on the dimensions of the barrier device as well as the intended use of the barrier device.

The barrier device can also include one or more anchoring support elements that reinforce the device at locations where the device is anchored to the soft tissue of the patient. The anchoring support elements improve internal hole stability, resistance to hole elongation, disruption, or tearing, and resistance to material separation from support tissue while also healing the underlying tissue. The barrier device of the present invention is implantable in a patient for short term or long term applications, and can include controlled release of the therapeutic agent.

There are a number of terms and phrases utilized herein that are well understood by those of ordinary skill in the art. Additional clarification and confirmation of some of these terms and phrases is provided immediately below and throughout this disclosure.

The term "sheet" as utilized herein generally refers to a mesh structure that is a relatively thin, surface, layer, or covering. A sheet may have a generally planar configuration or may have a contoured or otherwise irregular or non-planar configuration, including being formed, or being a shaped form.

The term "edge(s)" generally refers to a point or portion on a perimeter of a structure. Edges, therefore, define the perimeter of a structure. As one example, a square has four edges where the edges form the perimeter of the square. As another example, an edge of a circle is located on the perimeter along the circumference of the circle. As such, a line extending from the center of a circle to the perimeter has an end point that is in contact with an edge of the circle.

The term "bio-absorbable" generally refers to having the property or characteristic of being able to penetrate the tissue of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes, in a manner that does not result in cellular uptake of the biodegradable substance. Biodegradation thus relates to the breaking down and distributing of a substance through the patient's body, versus the consumption by or penetration into the localized cells of the patient's body tissue. Biodegradable substances, such as polymers, can cause inflammatory response due to either the parent substance or those substances formed during breakdown, and they may or may not be absorbed by tissues. Bio-absorbable substances break down into substances or components that do not cause an inflammatory response and can be consumed by the cells forming the body tissues.

The phrase "controlled release" generally refers to the release of a biologically active agent in a predictable manner over a desired period of time. Controlled release includes the provision of an initial burst of release upon implantation, followed by the predictable release over the predetermined time period. Accordingly, controlled release includes such embodiments as those that release substantially all or a significant portion of the biologically active agent in a predictable manner, and a substantially lesser amount of the biologically active agent for a duration thereafter. Additional embodiments include delivery of a biologically active agent to a targeted location along with the bio-absorbable gel components at the cellular level It should be noted that the phrase "cross-linked gel", as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration that can reversibly convert into oil compounds. In various preferred embodiments, the oil composition comprises a fatty acid molecule, a glyceride, and combinations thereof.

Furthermore, "curing" with respect to the present invention generally refers to thickening, hardening, or drying of a material brought about by heat, UV light, chemical means, reaction with biologically active agent and/or reactive gasses.

Modulated healing can be described as the in-vivo effect observed post-implant in which the biological response is altered resulting in a significant reduction in foreign body response. As utilized herein, the phrase "modulated healing" and variants of this language generally refers to the modulation (e.g., alteration, delay, retardation, reduction, detaining) of a process involving different cascades or sequences of naturally occurring tissue repair in response to localized tissue injury, substantially reducing their inflammatory effect. Modulated healing encompasses many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other. For example, the bio-absorbable oils described herein can alter, delay, retard, reduce, and/or detain one or more of the phases associated with healing of vascular injury caused by medical procedures, including, but not limited to, the inflammatory phase (e.g., platelet or fibrin deposition), and the proliferative phase. In one embodiment, "modulated healing" refers to the ability of a non-polymeric bio-absorbable cross-linked gel to alter a substantial inflammatory phase (e.g., platelet or fibrin deposition) at the beginning of the tissue healing process. As used herein, the phrase "alter a substantial inflammatory phase" refers to the ability of the non-polymeric bio-absorbable cross-linked gel to substantially reduce the inflammatory response at an injury site. In such an instance, a minor amount of inflammation may ensue in response to tissue injury, but this level of inflammation response, e.g., platelet and/or fibrin deposition, is substantially reduced when compared to inflammation that takes place in the absence of the non-polymeric bio-absorbable cross-linked gel.

For example, the non-polymeric bio-absorbable cross-linked gel of the present invention has been shown experimentally in animal models to delay or alter the inflammatory response associated with vascular injury, as well as excessive formation of connective fibrous tissue following tissue injury. The non-polymeric bio-absorbable cross-linked gel of the present invention has also been shown experimentally in animal models to delay or reduce fibrin deposition and platelet attachment to a blood contact surface following vascular injury. Additionally, experiments have shown that the non-polymeric bio-absorbable cross-linked gel of the present invention has resulted in a less dense, but uniformly confluent cellular overgrowth of a porous implanted mesh structure with little to no fibrous capsule formation.

Accordingly, the non-polymeric bio-absorbable cross-linked gel of the present invention provides an excellent absorbable cellular interface suitable for use with a surgical instrument or medical device that results in a modulated healing effect, avoiding the generation of scar tissue and promoting the formation of healthy tissue at a modulated or delayed period in time following the injury. Without being bound by theory, this modulated healing effect can be attributed to the modulation (e.g., alteration, delay, retardation, reduction, detaining) of any of the molecular processes associated with the healing processes of vascular injury. For example, the non-polymeric bio-absorbable cross-linked gel of the present invention can act as a barrier or blocking layer between a medical device implant (e.g., a surgical mesh, graft, or stent), or surgical instrument, and the cells and proteins that compose the vessel wall, such as the endothelial cells and smooth muscle cells that line the vessel's interior surface. The barrier layer prevents the interaction between the surgical implant and the vessel surface, thereby preventing the initiation of the healing process by the cells and proteins of the vessel wall. In this respect, the barrier layer acts as a patch that binds to the vessel wall and blocks cells and proteins of the vessel wall from recognizing the surgical implant (i.e., the barrier layer blocks cell-device and/or protein-device interactions), thereby blocking the initiation of the vascular healing process, and avoiding the fibrin activation and deposition and platelet activation and deposition.

In another non-binding example, the modulated healing effect can be attributed to the modulation (e.g., alteration, delay, retardation, reduction, detaining) of signaling between the cells and proteins that compose the vessel wall and various components of the bloodstream that would otherwise initiate the vascular healing process. Stated differently, at the site of vascular injury, the non-polymeric bio-absorbable cross-linked gel of the present invention can modulate the interaction of cells of the vessel wall, such as endothelial cells and/or smooth muscle cells, with other cells and/or proteins of the blood that would otherwise interact with the damaged cells to initiate the healing process. Additionally, at the site of vascular injury, the non-polymeric bio-absorbable cross-linked gel of the present invention can modulate the interaction of proteins of the vessel wall with other cells and/or proteins of the blood, thereby modulating the healing process.

When the non-polymeric bio-absorbable cross-linked gel of the present invention is being used as a barrier or blocking layer between a medical device implant (e.g., a surgical mesh, graft, or stent), or surgical instrument, and the cells and proteins that compose the tissue wall, the bio-absorbable cross-linked gel can be designed to maintain its integrity for a desired period of time, and then begin to dissolve and be absorbed into the tissue that it is surrounded by. Alternatively, the bio-absorbable cross-linked gel can be designed such that, to some degree, it is absorbed into surrounding tissue immediately after the medical device implant is inserted in the subject. Depending on the formulation of the non-polymeric bio-absorbable cross-linked gel that makes up the barrier layer, the barrier layer is completely absorbed into surrounding tissue within a time period of 1 day to 24 months, e.g., 1 week to 12 months, e.g., 1 month to 10 months, e.g., 3 months to 6 months. Animal studies have shown resorption of the barrier layer occurring upon implantation and continuing over a 3 to 6 month period, and beyond.

The oil component of the non-polymeric bio-absorbable cross-linked gel present invention can be either an oil, or an oil composition. The oil component can be a naturally occurring oil, such as fish oil, cod liver oil, cranberry oil, or other oils having desired characteristics. One example embodiment of the present invention makes use of a fish oil in part because of the high content of omega-3 fatty acids, which provide healing support for damaged tissue, as discussed below. The fish oil also serves as an adhesion-limiting agent. In addition, the fish oil maintains anti-inflammatory, non-inflammatory, or "modulated healing" properties as well. The present invention is not limited to with the use of fish oil as the naturally occurring oil for the non-polymeric bio-absorbable cross-linked gel. However, the description herein makes reference to the use of fish oil as one example embodiment. Other naturally occurring oils can be utilized in accordance with the present invention as described herein.

To understand further how the non-polymeric bio-absorbable cross-linked gel of the present invention functions, a brief discussion is provided below concerning tissue injury and healing generally. Vascular injury causing intimal thickening can be broadly categorized as being either biologically or mechanically induced. Biologically mediated vascular injury includes, but is not limited to, injury attributed to infectious disorders including endotoxins and herpes viruses, such as cytomegalovirus; metabolic disorders, such as atherosclerosis; and vascular injury resulting from hypothermia, and irradiation. Mechanically mediated vascular injury includes, but is not limited to, vascular injury caused by catheterization procedures or vascular scraping procedures, such as percutaneous transluminal coronary angioplasty; vascular surgery; transplantation surgery; laser treatment; and other invasive procedures which disrupt the integrity of the vascular intima or endothelium. Generally, neointima formation is a healing response to a vascular injury.

Wound healing upon vascular injury, and generally in non-vascular locations, occurs in several stages. The first stage is the inflammatory phase. The inflammatory phase is characterized by hemostasis and inflammation. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, which are potent vasoconstrictors. This initial response helps to limit hemorrhage. After a short period, capillary vasodilatation occurs secondarily to local histamine release, and the cells of inflammation are able to migrate to the wound bed. The timeline for cell migration in a normal wound healing process is predictable. Platelets, the first response cells, release multiple chemokines, including epidermal growth factor (EGF), fibronectin, fibrinogen, histamine, platelet-derived growth factor (PDGF), serotonin, and von Willebrand factor. These factors help stabilize the wound through clot formation. These mediators act to control bleeding and limit the extent of injury. Platelet degranulation also activates the complement cascade, specifically C5a, which is a potent chemoattractant for neutrophils.

As the inflammatory phase continues, more immune response cells migrate to the wound. The second response cell to migrate to the wound, the neutrophil, is responsible for debris scavenging, complement-mediated opsonization of bacteria, and bacteria destruction via oxidative burst mechanisms (i.e., superoxide and hydrogen peroxide formation). The neutrophils kill bacteria and decontaminate the wound from foreign debris.

The next cells present in the wound are the leukocytes and the macrophages (monocytes). The macrophage, referred to as the orchestrator, is essential for wound healing. Numerous enzymes and cytokines are secreted by the macrophage. These include collagenases, which debride the wound; interleukins and tumor necrosis factor (TNF), which stimulate fibroblasts (produce collagen) and promote angiogenesis; and transforming growth factor (TGF), which stimulates keratinocytes. This step marks the transition into the process of tissue reconstruction, i.e., the proliferative phase.

The second stage of wound healing is the proliferative phase. Epithelialization, angiogenesis, granulation tissue formation, and collagen deposition are the principal steps in this anabolic portion of wound healing. Epithelialization occurs early in wound repair. At the edges of wounds, epidermis immediately begins thickening. Marginal basal cells begin to migrate across the wound along fibrin strands stopping when they contact each other (contact inhibition). Within the first 48 hours after injury, the entire wound is epithelialized. Layering of epithelialization is re-established. The depths of the wound at this point contain inflammatory cells and fibrin strands. Aging effects are important in wound healing as many, if not most, problem wounds occur in an older population. For example, cells from older patients are less likely to proliferate and have shorter life spans and cells from older patients are less responsive to cytokines.

Heart disease can be caused by a partial vascular occlusion of the blood vessels that supply the heart, which is preceded by intimal smooth muscle cell hyperplasia. The underlying cause of the intimal smooth muscle cell hyperplasia is vascular smooth muscle injury and disruption of the integrity of the endothelial lining. Intimal thickening following arterial injury can be divided into three sequential steps: 1) initiation of smooth muscle cell proliferation following vascular injury, 2) smooth muscle cell migration to the intima, and 3) further proliferation of smooth muscle cells in the intima with deposition of matrix. Investigations of the pathogenesis of intimal thickening have shown that, following arterial injury, platelets, endothelial cells, macrophages and smooth muscle cells release paracrine and autocrine growth factors (such as platelet derived growth factor, epidermal growth factor, insulin-like growth factor, and transforming growth factor) and cytokines that result in the smooth muscle cell proliferation and migration. T-cells and macrophages also migrate into the neointima. This cascade of events is not limited to arterial injury, but also occurs following injury to veins and arterioles. Accordingly, the non-polymeric bio-absorbable cross-linked gels of the present invention are able to modulate (e.g., alter, delay or prevent) one or more of the steps associated with intimal thickening following arterial injury, thereby preventing the heart disease and further vascular injury associated with vascular medical procedures.

Chronic inflammation, or granulomatous inflammation, can cause further complications during the healing of vascular injury. Granulomas are aggregates of particular types of chronic inflammatory cells which form nodules in the millimeter size range. Granulomas may be confluent, forming larger areas. Essential components of a granuloma are collections of modified macrophages, termed epithelioid cells, usually with a surrounding zone of lymphocytes. Epithelioid cells are so named by tradition because of their histological resemblance to epithelial cells, but are not in fact epithelial; they are derived from blood monocytes, like all macrophages. Epithelioid cells are less phagocytic than other macrophages and appear to be modified for secretory functions. The full extent of their functions is still unclear. Macrophages in granulomas are commonly further modified to form multinucleate giant cells. These arise by fusion of epithelioid macrophages without nuclear or cellular division forming huge single cells which may contain dozens of nuclei. In some circumstances the nuclei are arranged round the periphery of the cell, termed a Langhans-type giant cell; in other circumstances the nuclei are randomly scattered throughout the cytoplasm (i.e., the foreign body type of giant cell which is formed in response to the presence of other indigestible foreign material in the tissue). Areas of granulomatous inflammation commonly undergo necrosis.

Formation of granulomatous inflammation seems to require the presence of indigestible foreign material (derived from bacteria or other sources) and/or a cell-mediated immune reaction against the injurious agent (type IV hypersensitivity reaction).

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha and gamma-tocopherols can be used alone or in combination to provide an effective transport of a given compound to a given cell target, region, or specific tissue location.

As described previously, the process of modulated healing and cellular remodeling with non-polymeric bio-absorbable cross-linked gels involves different cascades or sequences of naturally occurring tissue repair in response to localized tissue injury, and it encompasses many different biologic processes, including epithelial growth, inhibition, proliferation and/or differentiation, connective fibrous tissue production and function, angiogenesis, and several stages of acute and/or chronic inflammation. Therefore, for example, by using the non-polymeric bio-absorbable cross-linked gel of the invention, which have modulated healing characteristics, one or more of the cascades or sequences of naturally occurring tissue repair are modulated (e.g., delayed), resulting in long-term stabilization of the areas treated by, for example, the non-polymeric bio-absorbable cross-linked gel-coated devices. The reversibly cross-linked gel has been shown experimentally in animal models not to produce or induce a protracted inflammatory response and to delay healing or formation of connective fibrous tissue following tissue injury. As such, the non-polymeric bio-absorbable cross-linked gel of the present invention can delay fibrin and platelet activation associated with the initial phase of vascular healing, and this delay will result in a lower long-term risk of vascular injury due to the formation of vulnerable plaques associated with the initial fibrin and platelet activation. Accordingly, the non-polymeric bio-absorbable cross-linked gel of the present invention provides an excellent absorbable cellular interface suitable for use with a surgical instrument or implantable medical device.

It should be noted that as utilized herein, the non-polymeric bio-absorbable cross-linked gel of the invention includes fish oil, as well as fish oil fatty acid. As used herein, fish oil fatty acid includes, but is not limited to, omega-3 fatty acid, fish oil fatty acid, free fatty acid, monoglycerides, di-glycerides, or triglycerides, esters of fatty acids, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts thereof. Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The biocompatible oils, including fish oil, are cured as described herein to form a hydrophobic cross-linked gel.

Likewise, it should be noted that to the extent utilized herein to describe the present invention, the term "vitamin E" and the term "alpha and gamma-tocopherols", are intended to refer to the same or substantially similar substance, such that they are interchangeable and the use of one includes an implicit reference to both. Further included in association with the term vitamin E are such variations including but not limited to one or more of alpha and gamma-tocopherols, beta-tocopherol, delta-tocopherol, gamma-tocopherol, alpha-tocotrienol, beta-tocotrienol, delta-tocotrienol, gamma-tocotrienol, alpha and gamma-tocopherols acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha and gamma-tocopherols succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-cross linked semi-solid. Hydrogenation can reduce or eliminate omega-3 fatty acids and any therapeutic effects (both anti-inflammatory and wound healing) they offer.

For long term controlled release applications, synthetic polymers, as previously mentioned, have been utilized in combination with a therapeutic agent. Such a combination provides a platform for the controlled long term release of the therapeutic agent from a medical device. However, synthetic polymer coatings have been determined to cause inflammation in body tissue. Therefore, the polymer coatings often must include at least one therapeutic agent that has an anti-inflammatory effect to counter the inflammation caused by the polymer delivery agent. In addition, patients that receive a synthetic polymer coating based implant must also follow a course of systemic anti-inflammatory therapy, to offset the inflammatory properties of the non-absorbable polymer. Typical anti-inflammatory agents are immunosuppressants and systemic delivery of anti-inflammatory agents can sometimes lead to additional medical complications, such as infection or sepsis, which can lead to long term hospitalization or death. Use of the non-polymeric bio-absorbable cross-linked gel described herein can negate the necessity of anti-inflammatory therapy, and the corresponding related risks described, because there is no inflammatory reaction to the non-polymeric bio-absorbable cross-linked gel.

The term "barrier" or "barrier layer" is utilized to two primary ways in the present application. A "barrier layer" is intended to refer to a device that can be a stand-alone film or can be a coating or layer placed on another medical device. A "barrier layer device" is intended to relate to a device having a barrier layer coating applied thereto or encapsulating the underlying medical device, as later described herein.

FIGS. 1 through 16, wherein like parts are designated by like reference numerals throughout, illustrate example embodiments of non-polymeric biological and physical oil barrier layers and barrier devices according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 illustrates a non-polymeric biological oil barrier layer 10 in accordance with one embodiment of the present invention. The barrier layer 10 is flexible, to the extent that it can be placed in a flat, curved, or rolled, configuration within a patient. The barrier layer 10 is implantable, for both short term and long term applications. Depending on the particular formulation of the barrier layer 10, the barrier layer 10 will be present after implantation for a period of hours to days, weeks, or possibly months.

The barrier layer 10 is formed of an oil component. The oil component can be either an oil, or an oil composition. The oil component can be a naturally occurring oil, such as fish oil, cod liver oil, cranberry oil, or other oils having desired characteristics. One example embodiment of the present invention makes use of a fish oil in part because of the high content of omega-3 fatty acids, which provide healing support for damaged tissue, as discussed below. The fish oil also serves as an adhesion-limiting agent. In addition, the fish oil maintains anti-inflammatory or non-inflammatory properties as well. The present invention is not limited to formation of the film with fish oil as the naturally occurring oil. However, the following description makes reference to the use of fish oil as one example embodiment. Other naturally occurring oils can be utilized in accordance with the present invention as described herein.

It should further be noted that FIG. 1 represents merely one embodiment of the barrier layer 10. The barrier layer 10 serves as a biological oil barrier and, depending on degree of cure, can also serve as a physical barrier, as depicted. The biological oil barrier is represented by the application of the fatty acid based oil, such as fish oil, onto a medical device. Such a configuration provides a biological oil barrier layer that provides a non-inflammatory or anti-inflammatory barrier coating. Using a number of different methods as described below, the biological oil can be cured to create a non-polymeric cross-linked gel. In the instance of the medical device taking the form of a surgical mesh, the biological oil can be cured to the extent that the cells or pores of the mesh are substantially or completely bridged by the cured biological oil creating a physical barrier. With such a configuration there can remain some biological oil that is not cured but is inter-dispersed within the cured oil and maintains the biological oil barrier layer as well. Thus, substantial curing creates both a biological oil barrier layer and a physical barrier or tissue separating layer. The physical barrier provides modulated healing and adhesion-limiting properties of the barrier as discussed herein. Additional embodiments can include the provision of the substantially cured oil forming the biological oil barrier layer with physical layer, and then a subsequent application of the biological oil as a top coat. This creates a more substantial biological oil barrier layer supported by the combination biological oil barrier layer and physical barrier layer. Other embodiments can include the provision of a partially or substantially cured biological oil barrier layer that coats all or a portion of a surgical mesh without bridging the cells of the mesh. In such embodiments, the biological oil forms a barrier between the body tissue at the location of implantation and the physical structure of the mesh or other device.

One aspect of the barrier layer 10 mentioned above is that it has modulated healing and adhesion-limiting characteristics or properties. By adhesion-limiting, what is meant is a characteristic whereby the incidence, extent, and severity of postoperative adhesions induced by trauma, desiccational air injury, blunt dissection, or other lacerations or tissue injuries, between different tissue structures and organs and medical devices, is reduced (or changed). The adhesion-limiting characteristic of the present invention results from the bio-absorbable and non-polymeric materials used to form the barrier layer 10 surfaces.

More specifically, the barrier layer 10 provides a lubricious and/or physical non-adhesive surface against adhesion prone tissue. The barrier layer 10 itself, in its partially or substantially cured configuration, can provide a physical adhesion-limiting barrier between two sections of tissue, or the barrier layer 10 can form a modulated healing surface on a medical device, such as the mesh 40. The use of the naturally occurring oil, such as fish oil, either in its native state or when processed into a cross-linked gel or film coating provides an unexpected gliding surface against normally tacky moist tissue, which helps to reduce localized tissue abrasion injury and foreign body reaction. With less mechanical injury, there is less of an injury-induced inflammatory response, and less proliferative cell remodeling. The biological oil barrier created by the fatty acid oil derived barrier layer likewise provides anti-inflammatory and less tissue stimulating or biologically reactive properties, thus further reducing the occurrence of inflammatory response and adhesion related events due to inflammation. The surface of the barrier layer 10 provides the modulated healing and mechanical adhesion-limiting characteristics. One of ordinary skill in the art will appreciate that different oil chemistry makeup, ingredients, and blends will have different healthier stimulus, adhesive limited effects, or cellular response reaction properties. The fatty acids used to form the oils into the gel or film can be modified to be more liquefied, emulsified, softer, more rigid, or more gel-like, solid, or waxy, as desired. Accordingly, the degree of modulated healing response and/or adhesive limiting and tissue reactive properties offered by the barrier layer 10 can vary by modifying either the physical properties and/or chemical properties of the fatty acid containing oil. The modification of the oils from a more liquid physical state to a more gel-like or solid, but still flexible, physical state is further implemented through the curing process. As the oils are cured, especially in the case of fatty acid-based oils such as fish oil, reversible cross-links form creating a gel. As the curing process is performed over increasing time durations and/or increasing temperature or intensity conditions, more cross-links form transitioning the gel from a relatively wet liquid gel to a relatively solid-like, but still flexible, dry to the touch gel structure.

Another aspect of the present invention is that the barrier layer 10 can be formed of the bio-absorbable material, such as naturally occurring fish oil, in accordance with the example embodiment described herein. The bio-absorbable properties of the naturally occurring oil enable the barrier layer 10 to be absorbed slowly by the ingestion of the fatty acid components by cells of the body tissue (i.e., bio-absorbable). In example embodiments of the present invention, the bio-absorbable barrier layer contains lipids, many of which originate as triglycerides. It has previously been demonstrated that triglyceride byproducts, such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Other naturally occurring and synthetic oils, such as vitamin E compounds, can also integrate into cellular membranes resulting in decreased membrane fluidity and cellular uptake.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha and gamma-tocopherols can be used alone or in combination to provide an effective transport of a given compound to a given cell target, region, or specific tissue location. Both fatty acids and alpha and gamma-tocopherols can be incorporated into the barrier layer of the present invention described herein. Accordingly, fatty acids and alpha and gamma-tocopherols can be combined in differing amounts and ratios to contribute to a barrier layer in a manner that provides control over the cellular uptake characteristics of the barrier layer and any therapeutic agents mixed therein.

For example, the type, blend, or amount of alpha and gamma-tocopherols can be varied in the barrier layer. Alpha and gamma-tocopherols are known to slow autoxidation in fish oil by reducing hydro peroxide formation, which results in a decrease in the amount of cross-linking in cured fish oil. In addition alpha and gamma-tocopherols can be used to increase solubility of drugs in the fish oil forming the barrier layer. Thus, varying the amount of alpha and gamma-tocopherols present in the barrier layer can impact the resulting formation. Alpha and gamma-tocopherols have been determined experimentally to provide a synergistic protective effect to therapeutic drugs and compounds during curing, which increases the resulting drug load in the barrier layer after curing. Furthermore, with certain therapeutic drugs, the increase of alpha and gamma-tocopherols in combination with fatty acids in the barrier layer serves to slow and extend the rate of drug release due to the increased solubility of the drug in the alpha and gamma-tocopherols component of the barrier layer. This reflects the cellular uptake inhibitor functionality of alpha and gamma-tocopherol compounds, in that the localized delivery and cellular uptake of the drug can be further modulated or controlled, slowed, and extended over time during barrier layer surface absorption by the localized tissue.

It should further be emphasized that the bio-absorbable nature of the barrier layer results in the barrier layer 10 being completely absorbed through cell mediated fatty acid metabolic pathway over time by the localized cells in contact with the barrier layer. There are no known substances in the barrier layer surfaces, or break down byproducts of the barrier layer, that induce an inflammatory response during the naturally occurring fatty acid absorption process. The barrier layer 10 is generally composed of, or derived from, omega-3 fatty acids bound to triglycerides, potentially also including a mixture of free fatty acids and, depending upon the drug, options combinations with vitamin E (alpha and gamma-tocopherols). The triglycerides are broken down by lipases (enzymes) which result in free fatty acids that can than be transported across cell membranes. Subsequently, fatty acid metabolism by the cell occurs to metabolize any substances originating with the barrier layer. The bio-absorbable nature of the barrier layer of the present invention results in the barrier layer modulating healing and limiting adhesion formation while being completely absorbed over time, ultimately leaving only an underlying reinforced delivery or other medical device structure that is biocompatible. There is no known foreign body reaction or inflammatory response to the components forming the bio-absorbable barrier layer, or reinforced anchoring support elements.

Although the present invention is bio-absorbable to the extent that the barrier layer 10 experiences uptake and consumption into or through localized body tissues, in the specific embodiment described herein formed using naturally occurring oils, or synthetic equivalents, the exemplar oils are also lipid based oils. The lipid content of the oils provides a highly bio-absorbable barrier layer 10. More specifically, there is a phospholipids layer in each cell of the body tissue. The fish oil, and equivalent oils, contain lipids as well. There is a lipophilic action that results where the lipids are attracted by each other in an effort to escape the aqueous environment surrounding the lipids.

A further aspect of the barrier layer 10 is that the specific type of oil can be varied, and can contain elements beneficial to modulating healing. The barrier layer also breaks down during the absorption process into smaller fatty acid components, which can contributed to the localized tissue healing process involving cellular in-growth and remodeling of the barrier layer device. The addition of therapeutic agents to the barrier layer 10 component specifically for a localized drug delivery indication can be further utilized for additional beneficial biological effects, such as pain stimulation reduction or reduction in bacterial colonization, bio film formulation and adhesion, or localized infection minimization.

As described previously, the process of modulated healing and cellular remodeling, with barrier layer implants that include a reinforced anchoring support, involves different cascades or sequences of naturally occurring tissue repair in response to localized tissue injury, and it encompasses many different biologic processes, including epithelial growth, inhibition, proliferation and/or differentiation, connective fibrous tissue production and function, angiogenesis, and several stages of acute and/or chronic inflammation. The reversibly cross-linked gel of the barrier layer has been shown experimentally in animal models not to produce or induce a protracted inflammatory response and to delay healing or formation of connective fibrous tissue following tissue injury. Likewise, the reversibly cross-linked gel of the barrier layer has exhibited a complimentary or synergistic modulated healing effect, which results in a less dense, but uniformly confluent cellular overgrowth of a porous implanted mesh structure with little to no fibrous capsule formation, which is otherwise commonly seen with conventional permanent mechanical barrier devices. Accordingly, the cross-linked gel of the barrier layer 10 provides an excellent absorbable cellular interface suitable for use with a surgical implant with reinforced anchoring support.

Another aspect of the barrier layer 10 mentioned above is that the barrier layer 10 can contain therapeutic agents for local delivery to the body tissue in contact with the device. Therapeutic agents have been delivered to a localized target location within a human utilizing a number of different methods in the past. For example, agents may be delivered nasally, transdermally, intravenously, orally, or via other conventional systemic delivery methods. Local therapeutic delivery from a biological oil barrier layer device can be made to vary the therapeutic agent release rate (i.e., quick release or slow release) as part of the desired modulated healing effect of the barrier film surfaces.

As utilized herein, the phrase "therapeutic agent(s)" refers to a number of different drugs or biologically active agents available, as well as future agents that may be beneficial for use with the barrier layer of the present invention. Therapeutic agents can be added to the barrier layer 10, and/or the medical device in combination with the barrier layer 10 as discussed herein. The therapeutic agent component can take a number of different forms including additional modulated healing agents, adhesion-limiting agents, anti-oxidants, anti-inflammatory agents, anti-coagulant agents, thrombolysing agents, drugs to alter lipid metabolism, anti-proliferating agents, anti-neoplastics, tissue growth stimulants, functional protein/factor delivery agents, bactericidal agents, anti-biofilm adhesion agents, anti-infective agents, imaging agents, anesthetic agents, therapeutic agents, tissue absorption enhancers, antibiotics, germicides, anti-fungal agents, antiseptics, analgesics, prodrugs, and any additional desired therapeutic agents such as those listed in Table 1 below.

TABLE #1

| CLASS | EXAMPLES |
|---|---|
| Antioxidants | Alpha and gamma-tocopherols, fatty acids, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), fatty acids, leflunomide, NSAIDS, ibuprofen, acetaminophen, hydrocortizone acetate, hydrocortizone sodium phosphate, macrophage-targeted bisphosphonates, pimecrolimus, ISA247 |

TABLE #1-continued

| CLASS | EXAMPLES |
| --- | --- |
| Growth Factor Antagonists | Angiopeptin, trapidil, suramin |
| Antiplatelet Agents | Aspirin, fatty acids, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate, abcximab, viperinex, tenectaplase |
| Drugs to Alter Lipid Metabolism (e.g. statins) | Fluvastatin, fatty acids, alpha and gamma-tocopherols, fish oil, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, fatty acids, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine, SAR943, TAFA93 |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes, polymer surgical adhesives |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium., sirolimus, rapamycin, minocycline, rifampin, cephalosporin, cefipime, metronidazole |
| Gene Delivery | Genes for nitric oxide synthase, human growth hormone, antisense oligonucleotides |
| Local Tissue perfusion | Alcohol, H2O, saline, fish oils, vegetable oils, liposomes, fatty acid derived from fish oils, vitamin E |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium, MRI contrast agents, PET/CT contrast agents, ultrasound contrast agents, biomarker agents |
| Anesthetic Agents | Lidocaine, benzocaine, bupivacaine, levobupivacaine, ropivacaine, xylocaine |
| Descaling Agents | Nitric acid, acetic acid, hypochlorite |
| Anti-Fibrotic Agents | Interferon gamma-1b, Interluekin-10 |
| Immunosuppressive/Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase, cyclosporine |
| Tissue Absorption Enhancers | Fish oil, squid oil, omega 3 fatty acids, vegetable oils, lipophilic and hydrophilic solutions suitable for enhancing medication tissue absorption, distribution and permeation |
| Adhesion-limiting Agents | Hyaluronic acid, fatty acids, fish oil, vitamin E, human plasma derived surgical sealants, biodegradable hydrogels, surgical adhesives, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, silver acetate, sliver nitrate, furan derivatives, nitrofurazone, benzalkonium chloride, benzoic acid, salicylic acid, hypochlorites, peroxides, thiosulfates, salicylanilide |
| Antiseptics | Selenium, hydrogen peroxide |
| Analgesics | Bupivacaine, naproxen, ibuprofen, acetylsalicylic acid, levobupivacaine, ropivacaine, xylocaine |

Some specific examples of therapeutic agents useful in modulating or controlling localized tissue trauma response to cellular re-modeling with medical implants with barrier layers and/or modulated healing, and/or cellular proliferation involved in healing response include, modulated healing or anti-proliferating compounds including cerivastatin, cilostazol, fluvastatin, lovastatin, paclitaxel, pravastatin, m-Tor effecting compounds such as sirolimus, including, rapamycin, a rapamycin carbohydrate derivative (for example, as described in US Patent Application Publication 2004/0235762), a rapamycin derivative (for example, as described in U.S. Pat. No. 6,200,985), pro-drugs derived from rapamycin, analogs of rapamycin, including, everolimus, seco-rapamycin, seco-everolimus, and simvastatin. With systemic administration of such compounds orally, intravenously, or otherwise, the compounds are generally diluted throughout the body without specific localized delivery effect. There are drawbacks to a systemic delivery of a therapeutic agent, one of which is uncontrolled distribution that can occur when the therapeutic agent travels to all portions of the patient's body and creates undesired or unexpected effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher systemic dosing of the therapeutic agent.

Accordingly, an alternative to the systemic administration of a therapeutic agent is the use of a targeted local therapeutic agent delivery approach. With local delivery of a therapeutic agent, the therapeutic agent is administered using a medical device or apparatus (such as the barrier device of the present invention), directly by hand, or sprayed on the tissue, at a selected targeted tissue location of the patient that requires treatment. The therapeutic agent emits, or is otherwise delivered, from the medical device apparatus, and/or carrier (such as the barrier layer), and is applied to the targeted tissue location. The local delivery of a therapeutic agent enables a more concentrated and higher quantity of therapeutic agent to be delivered directly at the location of the implanted device, without having broader systemic distribution and potential remote target side effects.

Targeted local therapeutic agent delivery using a medical device with one or more barrier layers can be further broken into two categories, namely, short term and long term bioavailability to localized tissue ranging generally within a matter of seconds or minutes to a few days or weeks to a number of months. Conventionally, to achieve the long term bioavailability and delivery of a therapeutic agent to localized tissue, the therapeutic agent must be combined with a delivery agent, or otherwise formed with a physical impediment as a part of the medical device, to maximize absorption transfer of the therapeutic agent over an extended period of time while being absorbed by the local tissue.

Prior attempts to create surgically applied films and drug delivery platforms, such as in the field of soft tissue reinforcement, repair, or adhesion prevention, involving any soft tissue surgical intervention, make use of high molecular weight synthetic polymer base materials, including biodegradable and bio-erodable polymer films, non-absorbable polymer films, polymer gels and/or polymer coatings, to deliver therapeutic agents. Essentially, the polymer complexes in the platform release the drug or agent by allowing the drug to escape out from the polymer as it begins to dissolve at a predetermined rate once implanted at a location within the patient. Regardless of how beneficial to the local targeted tissue, most known polymer delivery materials release the therapeutic agent based release properties of the bulk polymer to elute the therapeutic agent or compound into adjacent or localized tissue and interstitial body fluids. Accordingly, the effect of the therapeutic agent is substantially local at the surface of the tissue making contact with the medical device having the coating. In some instances the effect of the therapeutic agent is further localized to the specific locations of, for example, stent struts or mesh that are anchored against the tissue location being treated. These prior approaches can create two different but undesirable local effects. One effect is the potential for an undesirable large quantity of drug into interstitial body fluids effecting bio-availability or cellular uptake of the drug, causing a localized or toxic effect. A second effect is an extended foreign body reaction to the carrier polymer after the therapeutic compound has been exhausted out of the polymer changing its local biochemical condition to adjacent tissue.

The barrier layer 10 of the present barrier device invention, however, makes use of biocompatible oils to form a non-polymeric bio-absorbable oil based therapeutic agent delivery platform, if desired. Furthermore, the barrier layer 10 can be formed in a manner that creates the potential for controlled long term release of a therapeutic agent, while still maintaining the modulated healing, adhesion-limiting, and/or anti-inflammatory benefits of the oil component of the barrier layer 10.

More specifically, it is known that oil that is oxygenated becomes a waxy solid. Attempts have been made to convert the polyunsaturated oils into a wax or solid to allow the oil to adhere to a device for a longer period of time. One such approach applies the oil to the medical device and allows the oil to dry.

With the present invention, and in the field of soft tissue reinforcement applications, and in part because of the lipophilic mechanism enabled by the bio-absorbable lipid based barrier layer 10 of the present invention, the uptake of the therapeutic agent is facilitated by the delivery of the therapeutic agent to the cell membrane by the bio-absorbable barrier layer 10, and not solely by drug release or elution out from the physical matrix used to form the barrier layer surfaces. Further, the therapeutic agent is not freely released into interstitial body fluids that are subject to systemic circulation, but rather, is delivered locally to the cells and tissue in contact with the barrier layer surfaces. In prior configurations using polymer based coatings, the once immobilized drugs or agents are released out from the polymer structure at a rate regardless of the reaction or need for the drug on the part of the cells receiving the drug.

In addition, the bio-absorbable oil used to form the barrier layer 10 is a naturally occurring oil, or synthetic equivalent, containing the omega-3 fatty acids (including DHA and EPA), and the process used for forming the barrier layer 10 of the present invention can be tailored to avoid causing detrimental effects to the beneficial properties of the omega-3 fatty acids, or at least effects too detrimental to have any lasting effect. Certain properties of the fatty acids may lose their effectiveness during curing, however other desired properties are maintained. Example embodiments illustrating the formation and different configurations of the barrier layer 10 are provided herein.

To summarize, the barrier layer 10 of the present invention serves as a non-polymeric biological oil barrier layer and can also serve as a therapeutically loadable physical barrier layer to modulate healing and/or limit adhesion formation to the device when sufficiently cured, altered chemically, and structured into a barrier layer. In accordance with the example embodiments described herein, the barrier layer is formed of a non-polymeric cross-linked gel, dry to the touch, which can be derived from fatty acid compounds. The fatty acids include omega-3 fatty acids when the oil utilized to form the barrier layer is fish oil or an analog or derivative thereof. As liquid pharmaceutical grade fish oil is heated, autoxidation occurs with the absorption of oxygen into the fish oil to create hydroperoxides in an amount dependent upon the amount of unsaturated (C═C) sites in the fish oil. However, the (C═C) bonds are not consumed in the initial reaction. Concurrent with the formation of hydroperoxides is the isomerization of (C═C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the barrier layer after the (C═C) bonds have substantially isomerized into the trans configuration. The (C═C) bonds can also form C—C cross-linking bridges in the glyceride hydrocarbon chains using a Diels-Alder Reaction. In addition to solidifying the barrier layer through cross-linking, both the hydroperoxide and (C═C) bonds can undergo secondary reactions converting them into lower molecular weight secondary oxidation byproducts including aldehydes, ketones, alcohols, fatty acids, esters, lactones, ethers, and hydrocarbons.

Accordingly, the barrier layer non-polymeric cross-linked gel derived from fatty acid compounds, such as those derived from fish oil, include a reversible cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. There are a substantial amount of ester bonds remaining after curing in addition to peroxide linkages forming the majority of the cross-links in the gel. The barrier layer converts into fatty acid, short and long chain alcohol, and glyceride molecules, which are all non-inflammatory and likewise consumable by cells in the soft tissue to which the barrier layer is applied. Thus, the barrier layer is bio-absorbable.

Figure 2A:
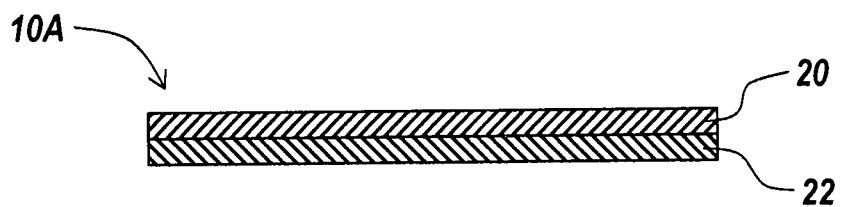
FIGS. 2A, 2B, and 2C are cross-sectional views of the barrier layer in accordance with one aspect of the present invention.
Figure 2B:
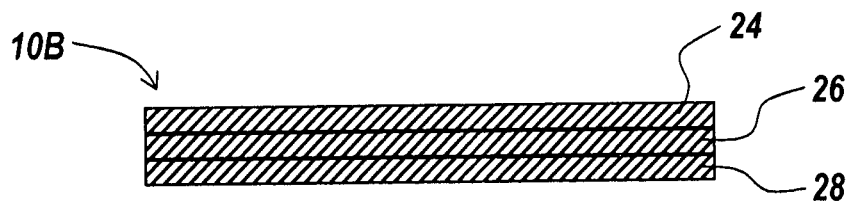
Figure 2C:
Figure 3A:
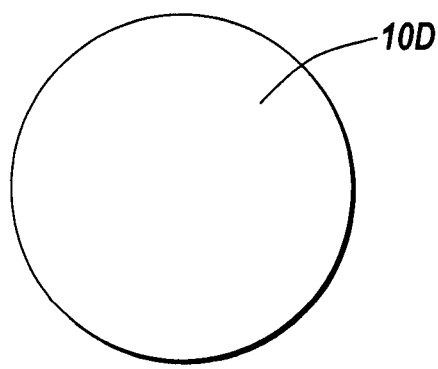
FIGS. 3A, 3B, 3C, 3D, 3E, and 3F are diagrammatic views of the barrier layer in accordance with another aspect of the present invention.
Figure 3B:
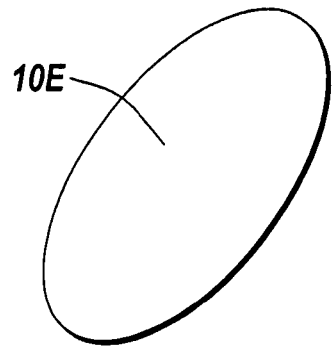
Figure 3C:
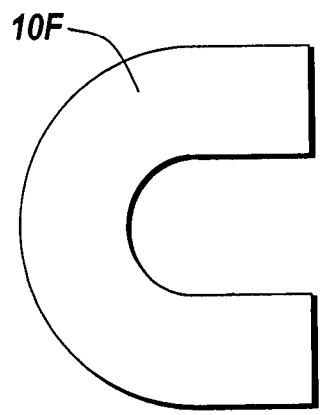
Figure 3D:
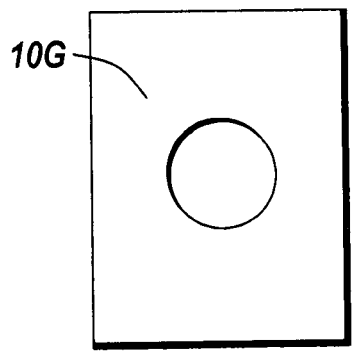
Figure 3E:
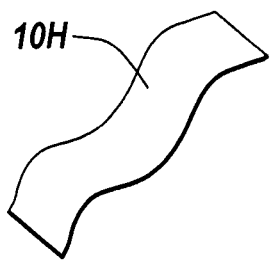
Figure 3F:
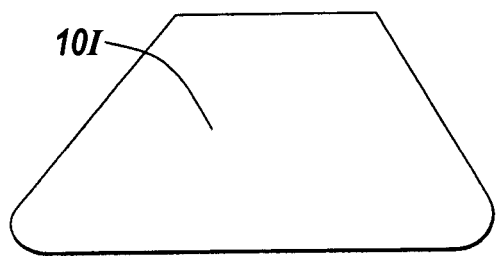

FIGS. 2A, 2B, and 2C illustrate side views of multiple different embodiments of the barrier layer 10 when cured into a flexible cross-linked gel. In FIG. 2A, a barrier layer 10A is shown having two tiers, a first tier 20 and a second tier 22. The first tier 20 and the second tier 22 as shown are formed of different materials. The different materials can be, for example, different forms of fish oil, different naturally occurring oils or biocompatible oils other than fish oil, or therapeutic components as will be discussed later herein. The different materials bind together to form the barrier layer 10A.

FIG. 2B shows a barrier layer 108 having a first tier 24, a second tier 26, and a third tier 28. In the illustrative embodiment shown, each of the tiers 24, 26, and 28 is formed of the same material. The plurality of tiers indicates the ability to create a thicker barrier layer 10 if desired. The greater the number of tiers, the thicker the resulting barrier layer. The thickness of the barrier layer 10 can have an effect on the overall strength and durability of the barrier layer 10. A thicker film can be made to be generally stronger and more durable, or can be made to be weaker and less durable, depending on the clinical application. In addition, the thickness of the barrier layer 10 can also affect the duration of time that the barrier layer 10 lasts and provides modulated healing or limited adhesion after implantation. A thicker barrier layer 10 provides more material to be absorbed by the body, and thus will last longer than a thinner barrier layer 10 of the same chemical makeup, which ultimately influences the implementation of the modulated healing. One of ordinary skill in the art will appreciate that the thickness of the barrier layer 10 can vary both by varying the thickness of each tier 24, 26, and 28, and by varying the number of tiers 24, 26, and 28. Accordingly, the present invention is not limited to the particular layer combinations illustrated.

FIG. 2C shows another barrier layer 10C, having four tiers, a first tier 30, a second tier 32, a third tier 34, and a fourth tier 36. In this example embodiment, the first tier 30 and the third tier 34 are formed of the same material, while the second tier 32 and the fourth tier 36 are formed of a material different from each other and different from that of the first tier 30 and the third tier 34. Accordingly, this embodiment illustrates the ability to change the number of tiers, as well as the material used to form each of the tiers 30, 32, 34, and 36. Again, the different materials can be derived from different forms of fish oil, different naturally occurring oils other than fish oil, or therapeutic components as will be discussed later herein.

FIGS. 3A through 3F show additional embodiments or configurations of the barrier layer 10. The embodiments include barrier layer 10D in a circular configuration, barrier layer 10E in an oval configuration, barrier layer 10F in a U-bend configuration, barrier layer 10G in a square configuration having a circular aperture, barrier layer 10H in a wave configuration, and barrier layer 10I in an irregular shape configuration. Each of the configurations of the barrier layer 10D through 10I represent different types of configurations. The configurations illustrated are by no means the only possible configurations for the barrier layer 10. One of ordinary skill in the art will appreciate that the specific shape or configuration of the barrier layer 10 can vary as desired and that the shapes and configurations depicted in FIG. 1 and FIGS. 3A through 3F are illustrative of only a small number of possible shapes and configuration.

Figure 4:
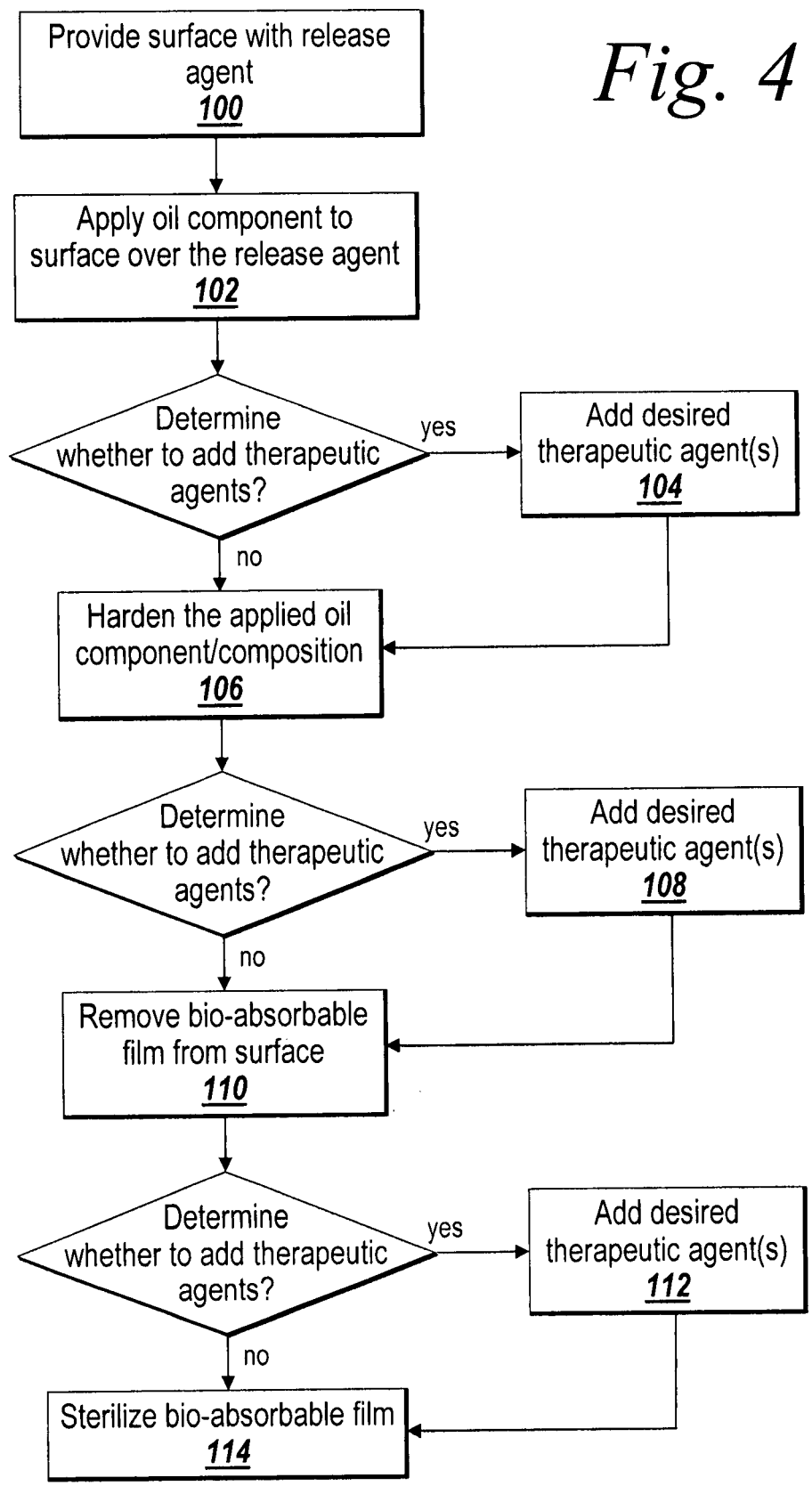
FIG. 4 is a flow chart illustrating a method of making the barrier layer of the present invention, in accordance with one embodiment of the present invention.

FIG. 4 is a flowchart illustrating one example method for the formation of the barrier layer 10. A surface is provided having a release agent (step 100). The surface can be prepared by the application of the release agent, or the release agent can be pre-existing. The release agent can be a number of different solutions, including for example, polyvinyl alcohol (PVA). The release agent can be applied in a number of different ways as well, including but not limited to casting, impregnating, spraying, dipping, coating, painting, and the like. It should be noted that the release agent can be applied optionally to the surface immediately prior to the remaining steps or well in advance of the remaining steps, so long as when the remaining steps are executed there is a release agent on the surface. It should further be noted that the need of an optional release agent can be eliminated if the surface itself has inherent characteristics similar to one having a release agent. Specifically, the surface can instead have a Teflon® coating, or other similar more permanent release surface. In such an instance, there is no need for a release agent, or subsequent removal of the release agent from the barrier layer formed.

An oil component is applied to the surface on top of the release agent (step 102). As noted previously, the oil component can be a naturally occurring oil, such as fish oil, cod liver oil, cranberry oil, or other oils having desired characteristics. In addition, the oil component can be an oil composition, meaning a composition containing oil in addition to other substances. For example, the oil composition can be formed of the oil component in addition to a solvent and/or a preservative. Solvents can include a number of different alternatives, including ethanol or N-Methyl-2-Pyrrolidone (NMP). The preservative can also include a number of different alternatives, including vitamin E. One of ordinary skill in the art will appreciate that there are a number of different solvents and preservatives available for use with the oil component to form the oil composition, and as such the present invention is not limited to only those listed in the examples herein. The solvent can be useful to alter the physical properties of the oil, as well as prepare the oil for combination with a therapeutic agent as described below. The preservative can also be useful in altering the physical properties of the oil component, as well as protecting some of the beneficial properties of the oil component during certain curing processes. Such beneficial properties include the healing and anti-inflammatory characteristics previously mentioned.

The oil component can be combined with one or more therapeutic agents to form an oil composition. Thus, if the added therapeutic benefit of a particular therapeutic agent or agents is desired, the therapeutic agent(s) can be added to the oil component prior to application to the surface, along with the oil component during application to the surface (including mixing with the oil component prior to application), or after the oil component has been applied (step 104). The different alternatives for adding the therapeutic agent(s) are determined in part based on the desired effect and in part on the particular therapeutic agent(s) being added. Some therapeutic agents may have reduced effect if present during a subsequent curing step. Some therapeutic agents may be more useful intermixed with the oil component to extend the release period, or applied to the surface of the oil component, resulting in a faster release because of increased exposure. One of ordinary skill in the art will appreciate that a number of different factors, such as those listed above in addition to others, can influence when in the process the therapeutic agent is added to the oil component, or the barrier layer 10. Accordingly, the present invention is not limited to the specific combinations described, but is intended to anticipate all such possible variations for adding the therapeutic agent(s).

For example, if 80% of a therapeutic agent is rendered ineffective during curing, the remaining 20% of therapeutic agent, combined with and delivered by the barrier can be efficacious in treating a medical disorder, and in some cases have a relatively greater therapeutic effect than the same quantity of agent delivered with a polymeric or other type of coating or barrier. This result can be modified with the variance of alpha and gamma-tocopherols to protect the therapeutic agent during the curing process, and then slow and extend the delivery of the therapeutic agent during absorption of the barrier layer into the tissue.

The oil component (or composition if mixed with other substances) is then hardened into the barrier layer 10 (step 106). The step of hardening can include hardening, or curing, such as by introduction of UV light, heat, oxygen or other reactive gases, chemical curing, or other curing or hardening method. The purpose of the hardening or curing is to transform the more liquid consistency of the oil component or oil composition into a more solid film, while still maintaining sufficient flexibility to allow bending and wrapping of the film as desired.

After the barrier layer 10 has formed, another determination is made as to whether therapeutic agents should be applied to the film. If desired, the therapeutic agent(s) is added to the barrier layer 10 (step 108). Subsequently, the barrier layer 10 is removed from the surface (step 110). Once again, there is opportunity to apply a therapeutic agent(s) to the barrier layer 10 on one or both sides of the barrier layer 10. If such therapeutic agent(s) is desired, the therapeutic agent(s) is applied (step 112). The additional therapeutic agent can also be applied in the form of a non-cured or minimally cured oil, such as fish oil. The oil can likewise include other therapeutic agents mixed therewith. The resulting structure of such an application forms the underlying barrier layer 10 that is cured to form the film, with a top coating of oil and potentially additional therapeutic agent layered on top. This structure enables the provision of a short term release of therapeutic from the oil top layer combined with a longer term release from the cured film, which takes more time to degrade.

After application of the therapeutic agent(s), or after the barrier layer 10 is removed from the surface, the barrier layer 10 is sterilized. The sterilization process can be implemented in a number of different ways. For example, sterilization can be implemented utilizing ethylene oxide, gamma radiation, E beam, steam, gas plasma, or vaporized hydrogen peroxide (VHP). One of ordinary skill in the art will appreciate that other sterilization processes can also be applied, and that those listed herein are merely examples of sterilization processes that result in a sterilization of the barrier layer 10, preferably without having a detrimental effect on the barrier layer.

It should be noted that the oil component or oil composition can be added multiple times to create multiple tiers in forming the barrier layer 10. For example, if a thicker barrier layer 10 is desired, additional tiers of the oil component or oil composition can be added after steps 100, 104, 106, 108, 110, or 112. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Figure 5A:
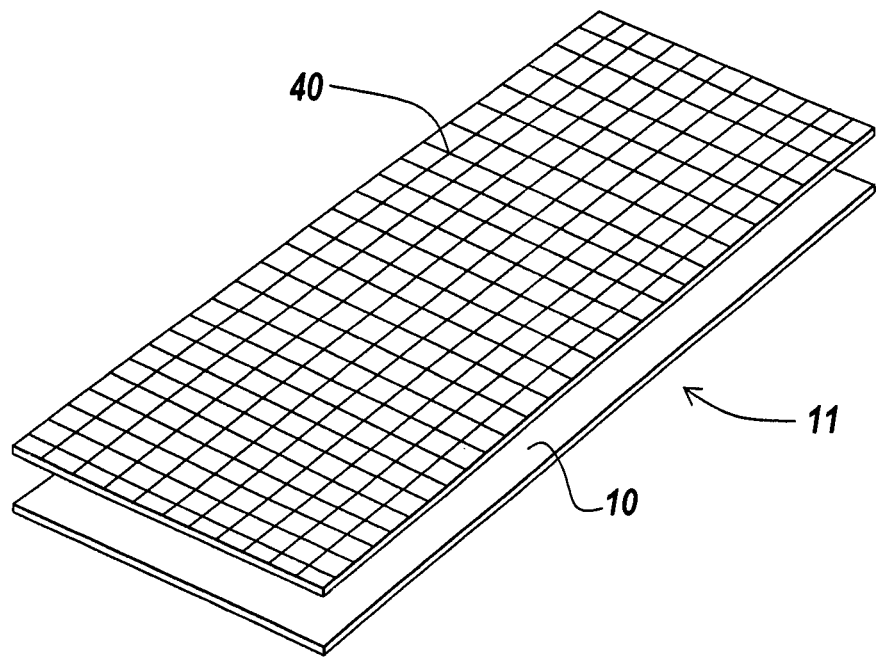
FIGS. 5A and 5B are perspective and cross-sectional views of the barrier layer in combination with a medical device, in accordance with one embodiment of the present invention.
Figure 5B:
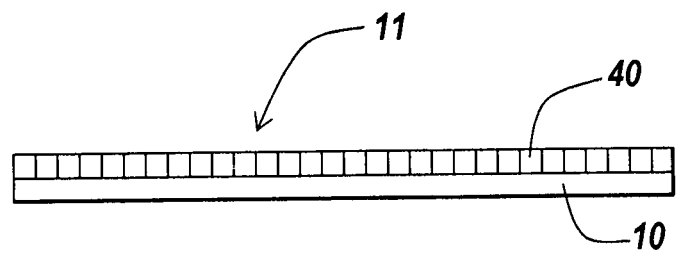

FIGS. 5A and 5B illustrate the barrier layer 10 and a medical device in the form of a generally flexible mesh 40 configured in sheet form, which together form a barrier device 11. In FIG. 5A, the barrier layer 10 and mesh 40 are shown in exploded view, while FIG. 5B shows the barrier layer 10 coupled with the mesh 40 to form the barrier device 11. The mesh 40 is merely one example medical device that can be entirely impregnated or 100% coupled with the barrier layer 10. In the instance of the mesh 40, it can be useful to have one side of the fully impregnated mesh support to be made having an, irregular or non-smooth surface to encourage faster or less delayed tissue in-growth, and the other side of the mesh with a smoother barrier layer 10. The smoother side of the barrier layer 10 can exhibit a more uniform tissue contacting support for gliding on tissue without dragging or pulling on the underlying tissue during installation, a smooth surface which limits the rate and/or attachment on adjacent tissue, a smooth surface which restricts the rate of in-growth, and provides improved adhesion-limiting, anti-inflammatory, and/or non-inflammatory surface properties. The coupling of the barrier layer 10 with the mesh 40 achieves such a device.

As understood by one of ordinary skill in the art, the properties of the mesh 40 and the barrier layer 10 can vary. There may be a requirement for the mesh 40 to have one side, or a portion of a side, that has adhesion-limiting properties for a period of several days. There may be a requirement for the mesh 40 to have one side, or a portion of a side, that has an irregular, non-smooth or thin barrier layer with mechanical or biochemical properties that last for a period of several hours to several days. As a further alternative, multiple locations on the mesh 40 may be required to have irregular, non-smooth, or roughened properties. As such, the barrier layer 10 can be applied to all sides, or portions of sides, or portions of one side of the mesh 40, whether it results in an irregular, smooth, bumpy, roughened, uniform, non-uniform, thickened, thin, or varying layer.

In addition, the requirement may be for the barrier layer adhesion-limiting, or reduced adhesion properties to last several weeks, several months, or even longer. Accordingly, the rate of degradation can also be varied by changing such properties as amount of readily reversible versus slow to reverse cross-linking, thickness, and existence of additives, such as vitamin E compounds (alpha and gamma-tocopherol) to achieve longer or shorter term adhesion-limiting and/or modulated healing properties. In addition, there may be a desire to include a therapeutic agent to further reduce inflammation, signaling via the mTOR pathway, or in selected clinical indications enhance cellular proliferation or speed up healing via the natural antigenic responding or inflammatory pathways, or to provide reduced localized pain stimulation at the site of the medical device fixation, or anchoring means, or to provide localized antibiotic delivery to reduce biofilm adhesion and biofilm formation, or anti-infective agent therapy, or other therapeutic measures, in combination with the use of the mesh 40. Accordingly, the therapeutic agent(s) can be added to the barrier layer 10, or coated thereon, or made mechanically different from location to location, to achieve the desired controlled release of the therapeutic agent after implantation. As previously described, combinations of various cure rates and methods used to apply the biological oils can be used, including for example one or more top coatings placed onto the barrier layer with lesser cured or non-cured oils with and/or without therapeutic agents made part of the barrier layer 10.

The particular properties or characteristics of the mesh 40 are determined based on the desired use of the mesh 40. A common implementation is for the mesh 40 to be formed of a bio-compatible material, such as polypropylene, however other bio-compatible materials can be utilized, such as a porous mesh or porous polymer film formed of the same or similar substance as the barrier layer 10 (i.e., oil based).

Figure 6:
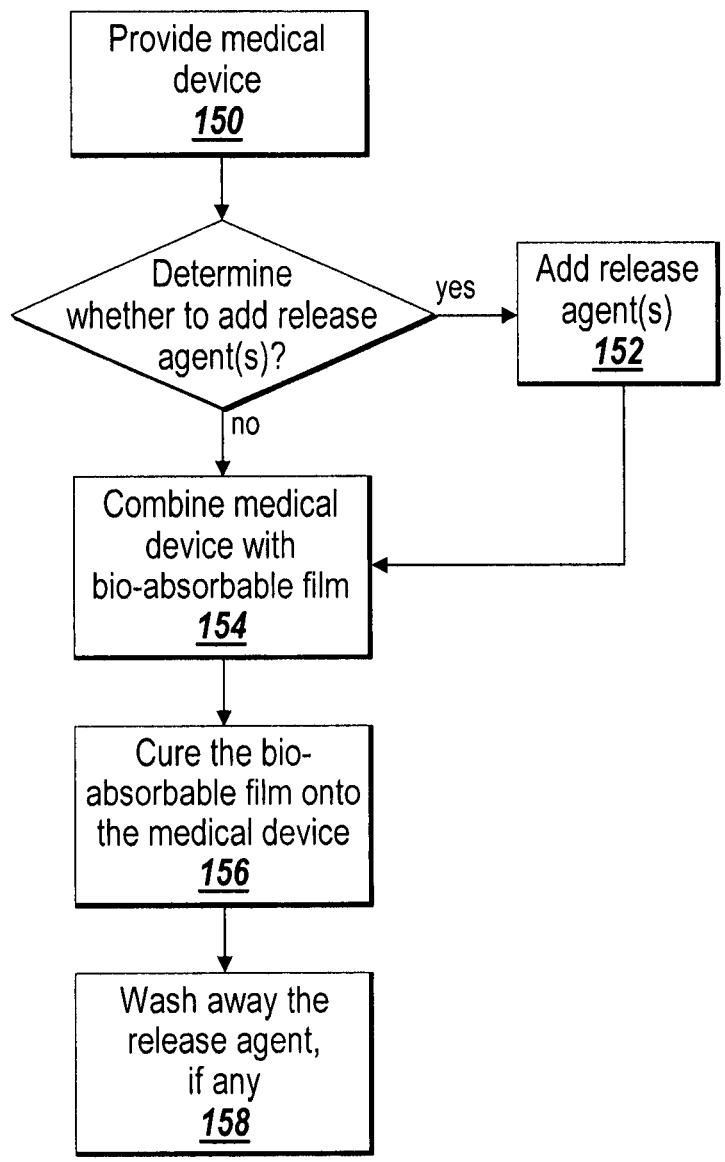
FIG. 6 is a flow chart illustrating a method of combining the barrier layer with a medical device, in accordance with one embodiment of the present invention.

FIG. 6 is a flowchart illustrating one example method for forming the medical device (i.e., mesh 40) and barrier layer 10 combination. The medical device is provided (step 150). The medical device can be, for example, the mesh 40.

A determination is made as to whether a release agent should be added to the medical device to aid in removing the device from its location (e.g., on a surface) after combination with the barrier layer 10. If a release agent is required, the release agent is applied to the medical device (step 152). An example release agent for such an application is polyvinyl alcohol.

The medical device is then combined with the barrier layer 10 (step 154). Depending on the particular medical device, the combination with the barrier layer 10 can be implemented more efficiently by either applying the barrier layer 10 to the medical device, or placing the medical device on the barrier layer 10. For example, in the case of the mesh 40, the mesh 40 can be placed on top of the barrier layer 10, or the barrier layer 10 can be placed on top of the mesh 40. Additionally, as discussed herein, the barrier layer 10 can be formed on or around the mesh 40 and in some instances can encapsulate the mesh 40.

The medical device and the barrier layer are then cured to create a bond (step 156). The curing process can be one of several known processes, including but not limited to applying heat, or UV light, or chemical curing, to cure the barrier layer. In the instance of the curing occurring with the liquid form of the barrier layer that is poured over and/or through the mesh, the curing creates a coating in and around the mesh 40, encapsulating the mesh within the barrier layer 10. After curing, if there is any release agent present, the release agent is washed away using water, or some other washing agent (step 158).

Figure 7:
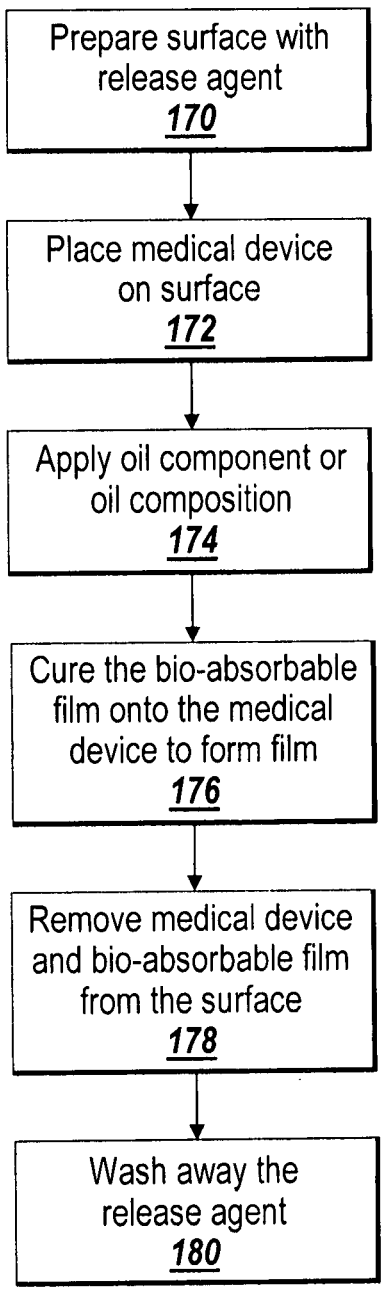
FIG. 7 is a flow chart illustrating another variation of the method of FIG. 6, in accordance with one embodiment of the present invention.

FIG. 7 is a flowchart illustrating another example method of forming a medical device with a barrier layer. A surface is prepared with a release agent, such as PVA (step 170), as needed. The medical device is placed on the surface (step 172). In the example embodiment, the medical device is the mesh 40. The oil component or oil composition is applied to the medical device (step 174). In the instance of the mesh 40, the oil component or oil composition is poured or sprayed onto the mesh 40. In such an embodiment the barrier layer 10 will fall substantially to a bottom side of the mesh 40 (due to gravitational pull), leaving a thinner coating or amount at a top side of the mesh 40, but still substantially encapsulating the mesh within the liquid of the barrier layer 10 material. Such a coating process provides for a barrier layer on all sides of the medical device (mesh 40). The combined oil component/composition and mesh 40 are then cured (step 176) using methods such as application of heat, UV light, oxygen and other reactive gases, chemical cross-linker, or hardening processes, to form the barrier layer in combination with the mesh 40. The combined barrier layer and mesh are then removed from the surface (step 178) and the release agent is washed away (step 180).

As with the method of FIG. 6, if desired, a therapeutic agent can be added to the oil component or oil composition at any point along the process forming the combined barrier layer 10 and mesh 40, including being a component of the oil composition. As discussed previously, consideration must be given as to whether the therapeutic agent may be affected by the curing process, or other aspects of the process.

Furthermore, the formation of the oil composition can be done in accordance with different alternatives to the methods described. For example, prior to forming the barrier layer 10, a preservative and/or compatibilizer, such as Vitamin E can be mixed with the oil component to form the oil composition. A solvent can be mixed with a therapeutic agent, and then added to the oil to form the oil composition. The solvent can be chosen from a number of different alternatives, including ethanol or N-Methyl-2-Pyrrolidone (NMP). The solvent can later be removed with vacuum or heat.

In addition, it should again be noted that the oil component or oil composition can be added multiple times to create multiple tiers in forming the barrier layer 10. If a thicker barrier layer 10 is desired, additional tiers of the oil component or oil composition can be added after steps 174 and 176. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Depending on the type of therapeutic agent component added to the barrier layer 10, the resulting barrier layer 10 can maintain its bio-absorbable characteristics if the therapeutic agent component is also bio-absorbable.

The therapeutic agent component, as described herein, has some form of therapeutic or biological effect. The oil component or oil composition component can also have a therapeutic or biological effect. Specifically, the barrier layer 10 (and its oil constituents) enable the cells of body tissue of a patient to absorb the barrier layer 10 itself, rather than breaking down the film and disbursing by-products of the film for ultimate elimination by the patient's body.

As previously stated, and in accordance with embodiments of the present invention, the barrier layer 10 is formed of a biocompatible oil, or composition including a naturally occurring oil, such as fish oil, cod liver oil, cranberry oil, and the like, or a synthetic oil including at least the required fatty acids and lipids in accordance with characteristics of the natural oils. A characteristic of the biocompatible oil is that the oil includes lipids, which contributes to the lipophilic action described later herein, that is helpful in the delivery of therapeutic agents to the cells of the body tissue. In addition, the biocompatible oil can include the essential omega-3 fatty acids in accordance with several embodiments of the present invention.

It should also be noted that the present description makes use of the mesh 40 as an example of a medical device that can be combined with the barrier layer 10 of the present invention. However, the present invention is not limited to use with the mesh 40. Instead, any number of other implantable medical devices can be combined with the barrier layer 10 in accordance with the teachings of the present invention. Such medical devices include catheters, grafts, balloons, prostheses, stents, other medical device implants, and the like. Furthermore, implantation refers to both temporarily implantable medical devices, as well as permanently implantable medical devices.

Figure 8A:
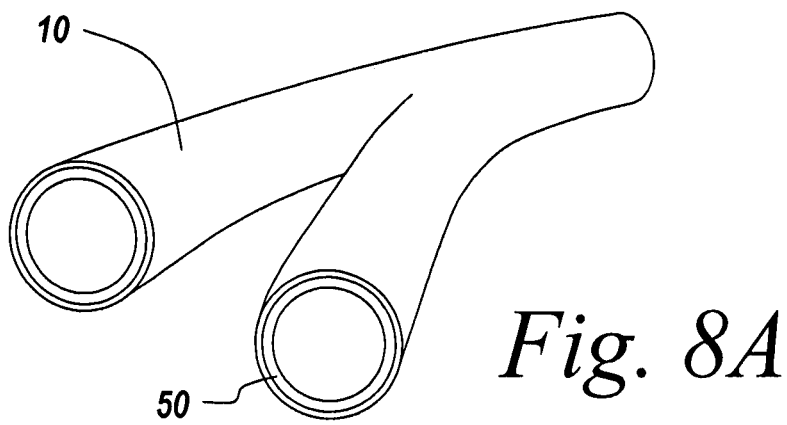
FIGS. 8A, 8B, and 8C are diagrammatic illustrations of the barrier coupled with various medical devices.
Figure 8B:
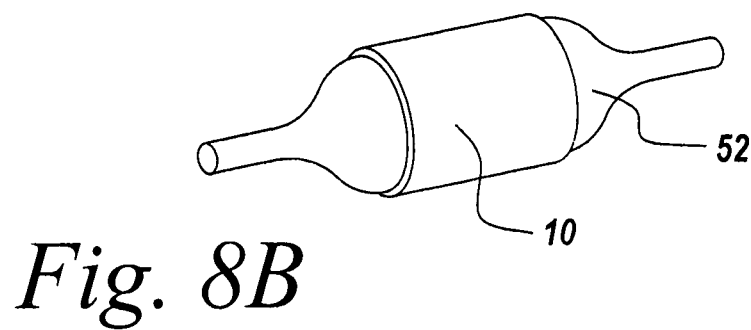
Figure 8C:
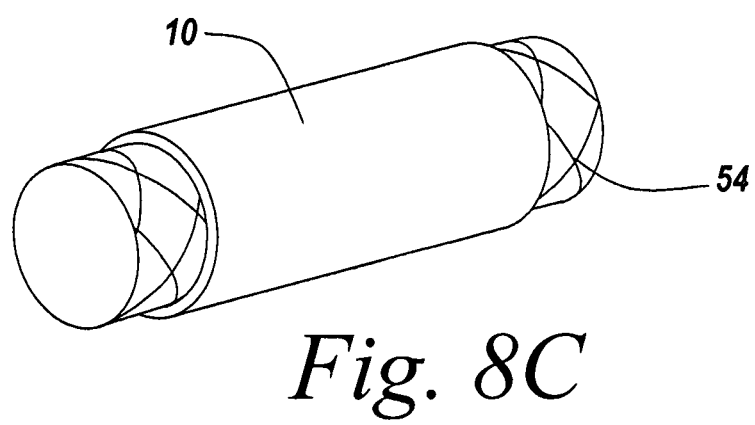

FIGS. 8A, 8B, and 8C illustrate some of the other forms of medical devices mentioned above in combination with the barrier layer 10 of the present invention. FIG. 8A shows a graft 50 with the barrier layer 10 coupled or adhered thereto. FIG. 8B shows a catheter balloon 52 with the barrier layer 10 coupled or adhered thereto. FIG. 8C shows a stent 54 with the barrier layer 10 coupled or adhered thereto. Each of the medical devices illustrated, in addition to others not specifically illustrated or discussed, can be combined with the barrier layer 10 using the methods described herein, or variations thereof. Accordingly, the present invention is not limited to the example embodiments illustrated. Rather the embodiments illustrated are merely example implementations of the present invention.

Figure 9:
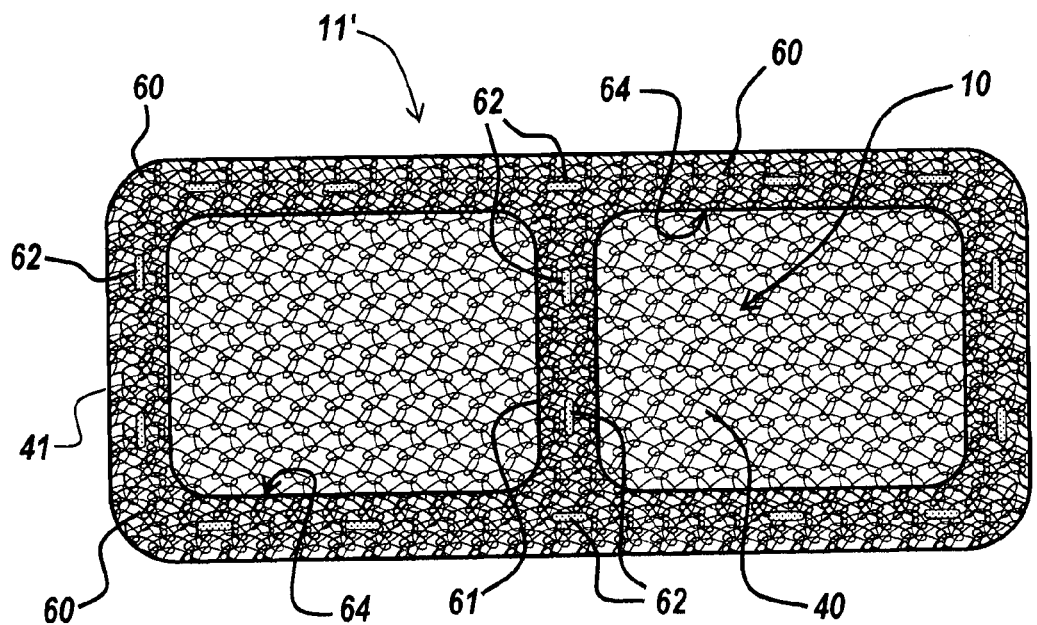
FIG. 9 is a diagrammatic illustration of a barrier device, formed of a mesh medical device in combination with the barrier layer, and further including a reinforcement element, in accordance with one embodiment of the present invention.
Figure 10:
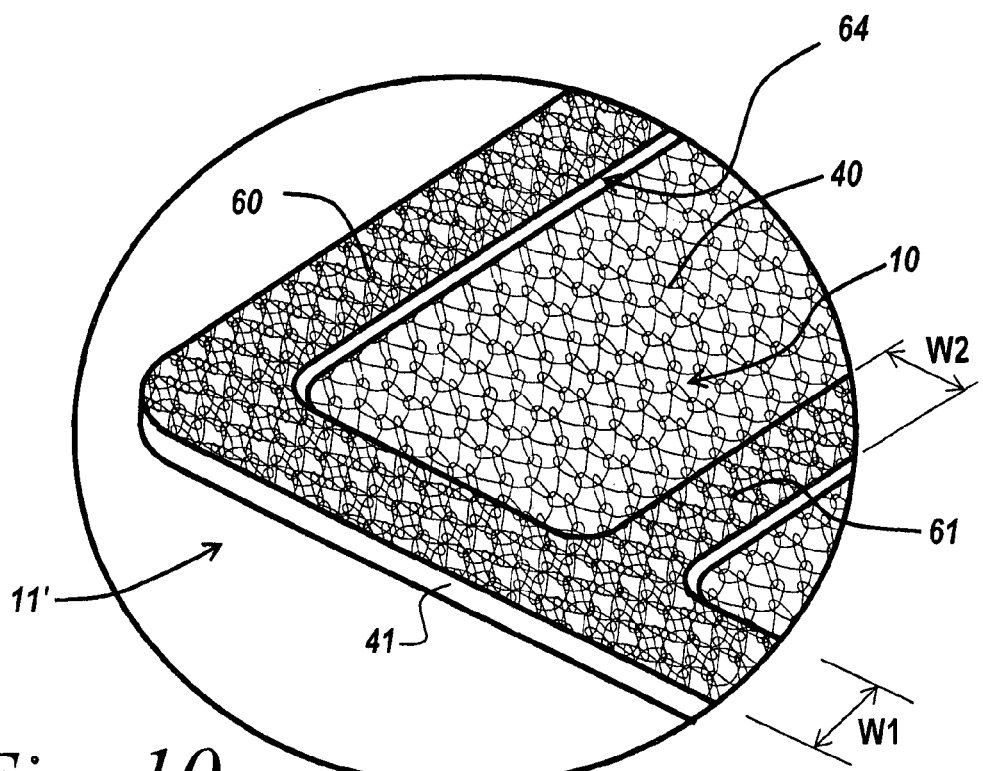
FIG. 10 is a zoomed in perspective illustration of a corner of the barrier device of FIG. 9, in accordance with one embodiment of the present invention.

In addition to the above-described configurations, the present invention can take the form of the barrier layer 10 formed with, or within, the medical device in the form of the mesh 40, with an anchoring support element 60 and/or one or more reinforcing support truss structures 61, to form a reinforced barrier device 11' having a modulated healing barrier surface, as depicted in FIGS. 9 and 10. In FIGS. 9 and 10, the barrier layer 10 and mesh 40 are shown with the barrier layer 10 coupled with the mesh 40. Again, the mesh 40 is merely one example medical device that can be coupled with the barrier layer 10. The mesh 40 can have one or more tissue contacting surfaces that exhibit a rougher surface to encourage tissue in-growth, and the opposite side of the mesh can have an adhesion-limiting, anti-inflammatory, and/or non-inflammatory surface or coating that is substantially smoother to prevent the mesh 40 from injuring surrounding tissue or causing inflammation. The smoother surfaces of the mesh 40 and barrier layer 10 combination act to delay healing, reduce adhesion formations, and are less disruptive, and more lubricious. It should additionally be noted that the mesh 40 and barrier layer 10 combination can further exhibit different surface topography, different surface gradients uniformity, and different levels of dryness, tackiness or smoothness properties. The barrier layer 10, in the example embodiment illustrated, is integrally coupled with the mesh 40 to the extent that the mesh 40 structure is fully enveloped or encapsulated within the barrier layer 10, and not merely coupled on one side of the mesh 40 with the barrier layer 10. As discussed below, this results in a thinner layer of the barrier layer 10 on a top side of the mesh 40 (as oriented during application of the barrier layer material) and a thicker layer of the barrier layer 10 occurring on a bottom side of the mesh 40; however the entirety of the mesh structure, if desired, is fully enveloped or encapsulated within a thin or thick layer of the barrier layer 10. The coupling of the barrier layer 10 with the mesh 40 achieves such a device.

The mesh 40 further includes the anchoring support element 60, which in the illustrative embodiment of the present figure is in the form of a frame of mesh that follows along the perimeter of the mesh 40. Thus, with a rectangular or oblong shaped mesh 40, the frame of the anchoring support element 60 is likewise rectangular or oblong in shape. One of ordinary skill in the art will appreciate that the shape of the anchoring support element 60 depends upon the shape of the underlying mesh 40 or desired anatomical application. Essentially, the function of the anchoring support element 60 is to provide added structural integrity and strength at the locations along which a surgeon is most likely to anchor, suture, or tack the reinforced barrier device 11' to soft tissue. Therefore, a border-like or perimeter frame, or perimeter patch-like structures having an approximate perimeter support ratio of about 3:5 (or 60%) or less is sufficient to provide adequate anchoring support. This perimeter support ratio can be calculated by determining the total area of the anchoring support element 60 and dividing it by the total area of the underlying mesh 40. The result is the ratio of about 3:5 (or 60%) or less. It should be noted, and as later discussed, the anchoring support element 60 can be continuous or can be discontinuous; it is the total area of any anchoring support element 60 components that is compared with the total area of the underlying mesh 40 that results in the perimeter support ratio determination. An anchoring support element 60 having approximately 0.25 inches to 1 inch of width (W1) extending from the edge of the mesh 40 is likely sufficient for many applications. However, it should be noted that this 0.25 inch to 1 inch dimension is merely exemplary of what may be a useful width. More importantly, the width (W1) of the anchoring support element 60 extending from the edge of the perimeter of the mesh 40 is best defined as that width dimension that is sufficient enough or required to provide enhanced strength, tear resistance, elongation prevention when implanted, and also to provide a surgeon or other medical user with adequate area to target for the insertion of anchors, sutures, tacks, adhesive, and the like, to hold the reinforced barrier device 11' in place in the patient. The duration of the anchoring function is preferably until modulated healing and cellular growth has transformed to a point whereby the underlying mesh 60 has become substantially healed or substantially incorporated with tissue to further anchor the underlying medical device and hold it in place. The additional layer of the anchoring support element 60 can be formed by either a separate layer or fold in the underlying mesh material, to significantly increase the strength and an aversion to tearing when apertures and/or button holes are created in the anchoring support element 60 and the mesh 40 to anchor the reinforced barrier device 11' in place. The additional layer of the anchoring support element 60 also significantly increases the resistance to tearing. The anchoring support element 60, while adding strength to the device, does not significantly alter the flexibility of the reinforced barrier device 11' relative to a single layer mesh 40 with barrier layer 10. Thus, the purpose of the anchoring support element 60 is not to rigidify the mesh 40 or the overall reinforced barrier device 11'. Instead, the anchoring support element 60 is sized and dimensioned to provide anchoring reinforcement at locations where apertures are formed, or attachments are made, to anchor the reinforced barrier device 11' in place during implantation, and after patient recovery.

The anchoring support element 60 can take a number of different structural forms, including the same structure as the underlying mesh 40, with the same orientation of grids, or with slightly out of phase alignment of the cells or grid of the mesh shape. In addition, the anchoring support element 60 can take other structural forms, such as a mesh with different sized and/or shaped mesh cells or pores, a more solid structural form, a denser weave, or a structure having more cells in its mesh shape than the underlying mesh 40, or made with variable surface finishes including smooth, rough or gradual finish features. In addition, the thickness and cross-sectional shape of each thread or bar forming the mesh of the anchoring support element 60 can likewise vary relative to the underlying mesh 40. Furthermore, the anchoring support element can have a different structure from a mesh structure, being more solid and more rigid.

The mesh 40 further includes one or more reinforcing support truss structures 61, which in the illustrative embodiment of the present figure is in the form of a mesh that extends between edges of a perimeter 41 of the mesh 40 and across the interior surface of the mesh 40. In some embodiments, the reinforcing support truss structure 61 can contact the perimeter 41. In other embodiments, the reinforcing support truss structure 61 does not contact the perimeter 41, but merely extends towards the perimeter 41. The shape, size (dimensions) of the one or more reinforcing support truss structures 61 can depend upon the shape, size and/or a desired anatomical application of the barrier device 11'. Essentially, the function of the one or more reinforcing support truss structures 61 is to provide added structural integrity and strength at the locations that experience stress during and/or after implantation as well as to add structural integrity and strength to the barrier device 11' itself for larger dimension applications. The width (W2) of the one or more reinforcing support truss structures 61 is chosen such that the one or more reinforcing support truss structures are sufficient to provide, in one or more dimensions or planes, enhanced strength, tear resistance, elongation prevention, etc., during and/or after implantation. In some instances, the width (W2) of the reinforcing support truss structure 61 can be substantially equal to the width (W1) of the anchoring support element 60. In other instances, the width (W2) of the reinforcing support truss structure 61 can be less than or greater than the width (W1) of the anchoring support element 60. The reinforcing support truss structure 61, while adding strength to the device and/or portions thereof, may or may not significantly alter the flexibility of the reinforced barrier device 11' relative to a single layer mesh 40 with barrier layer 10. The purpose, however, of the reinforcing support truss structure is not to rigidify the mesh 40, but to reinforce barrier device 11' and/or portions thereof at locations that are not anchored during and/or after implantation. In fact, the flexibility of the mesh 40 is substantially maintained.

For embodiments requiring a barrier device 11' having at least one dimension of three inches or larger, the use of reinforcing support truss structures 61 can become increasingly important. This may result because as the barrier device 11' increases in area, the area of the mesh 40 increases. Thus, while the anchor support element 60 may provide additional strength at locations of anchoring the barrier device 11', the unanchored portions of the barrier device 11' may not be sufficiently reinforced to withstand or reduce deformations from stresses, such as distortions or stretching, in one or more dimensions or planes. By including reinforcing support truss structure 61 in the barrier device 11', the barrier device 11' or portions thereof can be sufficiently reinforced to prevent or reduce deformations that can occur during and/or after implantation.

The reinforcing support truss structure 61 can take a number of different structural forms, including the same structure as the underlying mesh 40, with the same orientation of grids, or with slightly out of phase alignment of the cells or grid of the mesh shape. In addition, the reinforcing support truss structure 61 can take other structural forms, such as a mesh with different sized and/or shaped mesh cells or pores, a more solid structural form, a denser weave, or a structure having more cells in its mesh shape than the underlying mesh 40, or made with variable surface finishes including smooth, rough or gradual finish features. In addition, the thickness and cross-sectional shape of each thread or strand forming the mesh of the reinforcing support truss structure 61 can likewise vary relative to the underlying mesh 40. Furthermore, the reinforcing support truss structure 61 can have a different structure from a mesh structure, being more solid and/or more rigid.

In some embodiments the reinforcing support truss structure 61 and the anchor support element 60 can be composed of a single continuous structure, such as a single continuous portion of mesh. In other embodiments, the reinforcing support truss structure and the anchor support element may be separate components that are individual disposed or formed on the mesh 40. When the reinforcing support truss structure 61 and the anchor support element 60 are separate components, the reinforcing support truss structure and the anchor support element 60 can be composed of different structural forms. For example, the reinforcing support truss structure can be composed of a material that provides more rigidity than the anchor support element 60 and the anchor support element can be composed of a more flexible material that is more resistant to tearing than the material that composes the reinforcing support truss structure 61 or vice versa.

The reinforcing support truss structure and/or the anchoring support element 60 can be held together (permanently or temporarily) with the underlying mesh 40 prior to the application of the barrier layer 10 coating in order to hold the reinforcing support truss structure and/or the anchoring support element 60 in place during application of the barrier layer 10. For example, a plurality of permanent attachment welds 62 can be provided to join the reinforcing support truss structure 61 and the anchoring support element 60 with the mesh 40 by use of heat, pressure, and/or ultrasonic means. Alternatively, other fastening mechanisms, including temporary or permanent adhesive, or other welds (such as laser or chemical etching) can be utilized, so long as they are formed of biocompatible materials for embodiments relating to implantable devices.

In addition, it should be noted that the combination of the barrier layer 10 with the mesh 40, the anchoring support element 60, and the reinforcing support truss structure 61 creates a combination of components that together have increased strength while still maintaining a desired flexibility. The barrier layer 10, once cured, immobilizes the reinforcing support truss structure 61 and/or the anchoring support element 60 relative to the underlying mesh 40, such that there is no slippage or movement of the reinforcing support truss structure and/or the anchoring support element 60 relative to the mesh 40. This results in an increased strength of the combined components that is greater than any of the individual mesh 40, the reinforcing support truss structure 61, the anchoring support element 60, or barrier layer 10 coating independently. The immobilization of the components relative to each other increases the overall strength, while the overall structure remains flexible due primarily to the individual flexibilities of the cured barrier layer 10, the mesh 40, the reinforcing support truss structure 61 and the anchoring support element(s) 60.

Figure 11A:
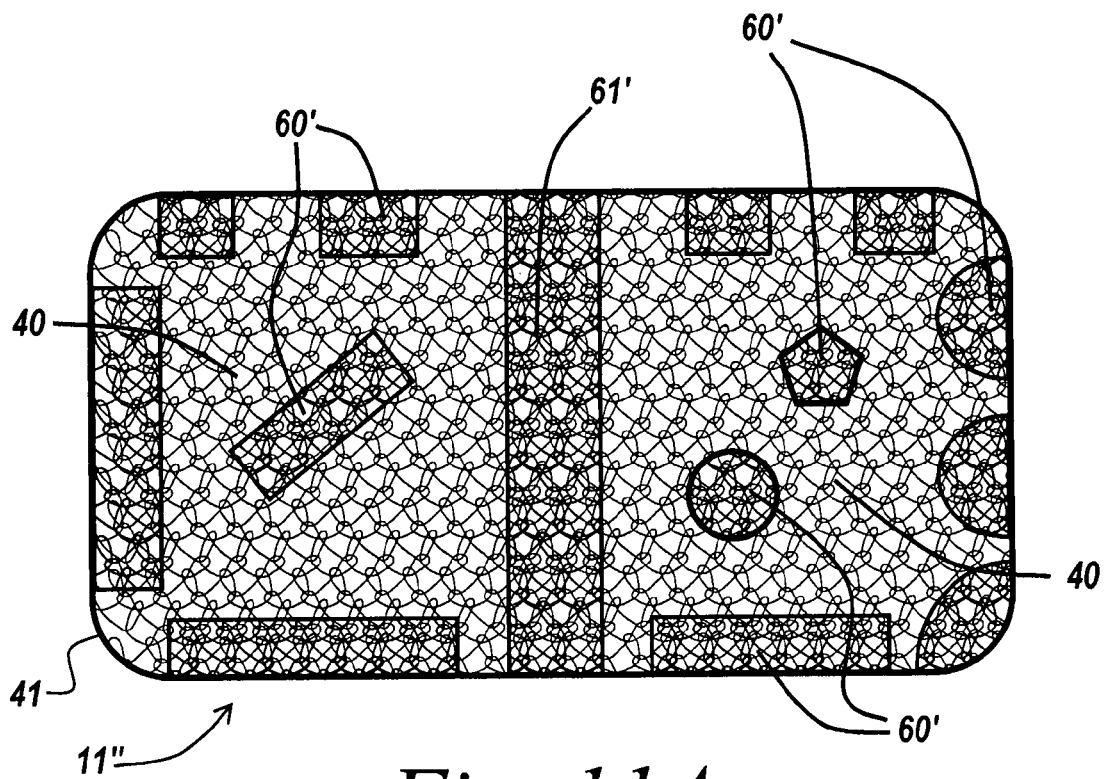
FIGS. 11A, 11B and 11C are a diagrammatic illustration of a barrier device demonstrating a variety of different reinforcement elements, in accordance with a plurality of embodiments of the present invention.

FIG. 11A is representative of a plurality of different shapes, sizes, and locations for the placement of a fragmented plurality of anchoring support elements 60' and one or more reinforcing support truss structures 61' used for barrier device 11". As illustrated, the anchoring support element 60' need not be in the shape of a perimeter frame. In particular, the anchoring support element 60' can have a number of different shapes, sizes, forms, symmetries, non-symmetries, and locations along the underlying mesh 40 structure. Ideally, if the frame structure of FIGS. 9 and 10 is not utilized, and instead some form or collection of anchoring support elements 60' is used, then each anchoring support element 60' should be placed at locations on the mesh 40 that would be likely locations for hosting or receiving a suture, tack, anchor, or adhesive. This can include locations anywhere along a perimeter 41 of the mesh 40, as well as locations found interior to the edge of the mesh 40.

The reinforcing one or more support structures 61' extend across an interior portion of the underlying mesh structure 40. The one or more support structures 61' can extend towards the perimeter 41. In some instances, such as the one depicted in FIG. 11A, the one or more support structures 61' can contact the perimeter of the underlying mesh 40. In other instances, the reinforcing support truss structure does not contact the perimeter of the underlying mesh structure 40.

Figure 11B:
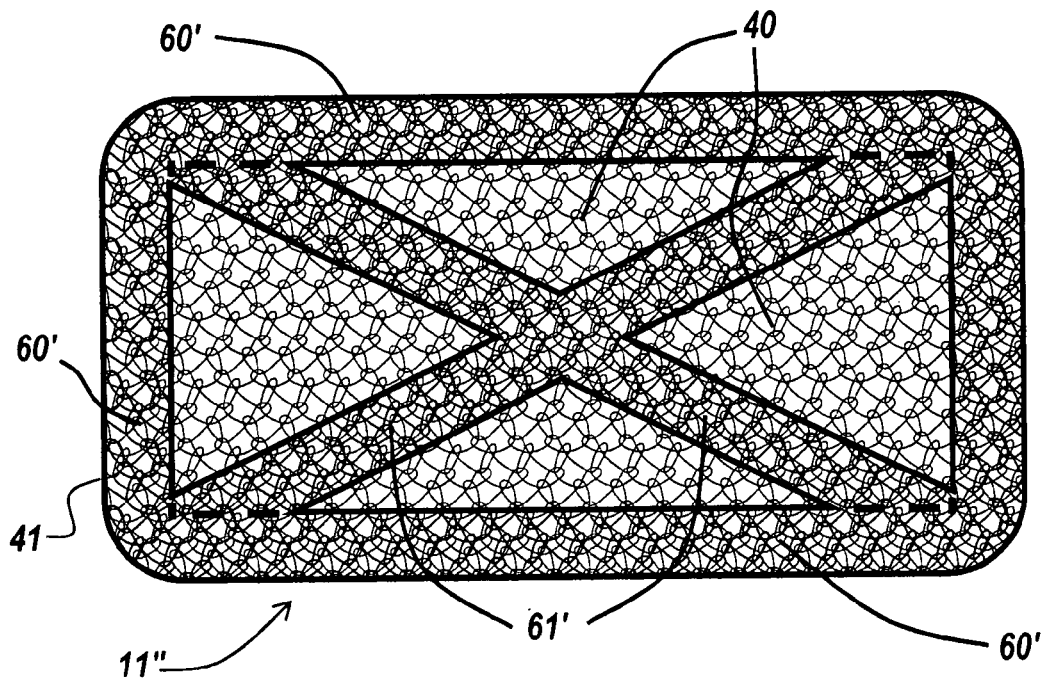
Figure 11C:
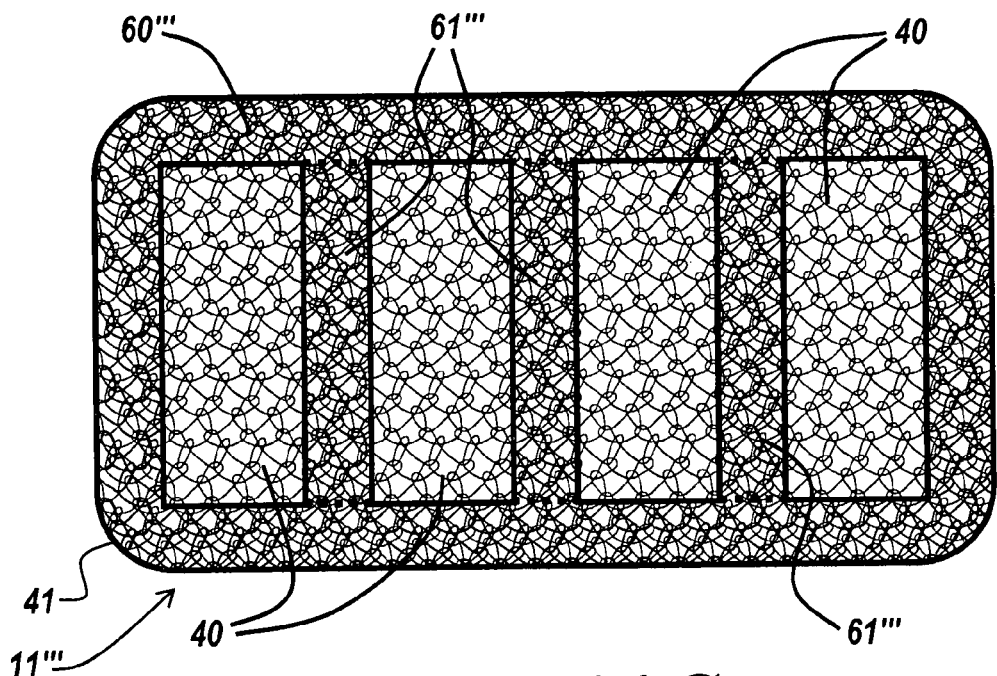

FIGS. 11B and 11C depict additional exemplary arrangements of the one or more reinforcing support truss structures 61". The one or more reinforcing support truss structures 61" can be arranged in any manner. The one or more reinforcing support truss structures 61" generally extend towards a perimeter 41 and across the interior of the barrier device 11'. The size and arrangement of the one or more support structures 61" can be related to the size, shape and anatomical application for the barrier device 11'''.

The location, layout, and configuration of the support structure(s) 61 is primarily determined by the need or desire to provide additional structural support to interior portions of the mesh 40 while maintaining as much of the flexibility of the mesh 40 as possible. As such, a balance must be struck between maintaining flexibility and tissue in-growth characteristics of the mesh 40, and providing necessary structure to avoid or reduce unwanted mesh deformation, including distortion or stretching. The size, shape and location of reinforcing support truss structure(s) 61 can vary to provide the additional structural support. When determining the size, shape and location of the reinforcing support truss structure(s) 61, the anatomical application, the size of the barrier device 11, the shape of the barrier device 11, etc., can be considered.

The above arrangements of the anchor support elements 60' and reinforcing support truss structures 61 in FIGS. 11A-C are illustrative and are not meant to be limiting. One of ordinary skill in the art would recognize that other arrangements may be implemented and that certain arrangements may be provided for specific anatomical applications.

Figure 12:
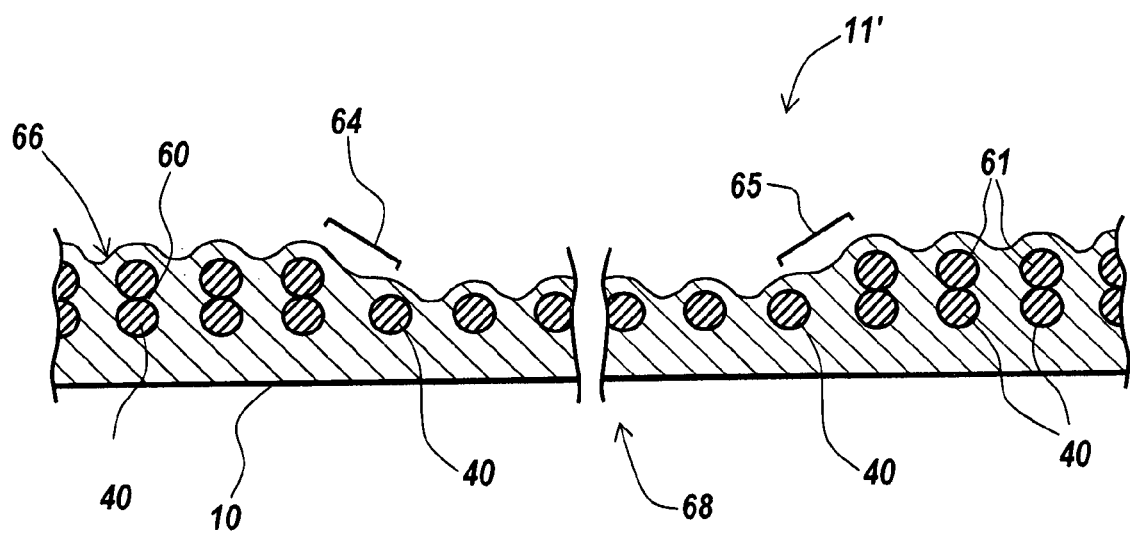
FIG. 12 is a cross-sectional illustration of the barrier device of FIG. 9, in accordance with one aspect of the present invention.

FIG. 12 is a cross-sectional view of the reinforced barrier device 11' of FIGS. 9 and 10, in accordance with one example embodiment. The reinforced barrier device 11' has the underlying mesh 40 structure with the anchoring support element 60 and the reinforcing support truss structure 61 disposed on the mesh 40 for a portion of the mesh 40 surface area. The mesh 40, the anchoring support element 60 and the reinforcing support truss structure 61 are encapsulated within the barrier layer 10, which in this embodiment is of the type described in the method of FIG. 7 herein, where an oil component or oil composition is applied to the mesh structure, falls substantially to a bottom side of the mesh 40 (due to gravitational pull) leaving a thinner coating or amount at a top side of the mesh 40, but still substantially encapsulating the mesh within the liquid of the barrier layer 10 material. The combined oil component/composition and mesh 40 are then cured to form the barrier layer 10 in combination with the mesh 40, i.e., the reinforced barrier device 11'. It should be noted that the barrier layer can be finished a number of different ways, including as an irregular roughened or non-smooth surface, as a smooth surface, or any combination of rough and smooth surface finishes, which impacts the degree of delay resulting in the modulated healing process, and also influences the limits placed on adhesion formations. As an example, when the surface thicker and smoother, the healing process requires a longer amount of time (increased degree of delay). As another example, when the surface is roughened, however, the surface provides an opportunity for the tissue to grow and heal because blood and fibrin can be deposited on the surface and can therefore reduce an amount of time necessary for healing (reduced degree of delay).

In one embodiment illustrated in FIG. 12, the barrier layer material is particularly proficient at smoothing out a transition 64 between the anchoring support element 60 and the underlying mesh 40 as well as a transition 65 between the reinforcing support truss structure 61 and the underlying mesh 40. As can be seen in FIG. 12, the transition 64 between the anchoring support element 60 and the mesh 40 and the transition 64 between the reinforcing support truss structure 61 and the mesh 40 are actually steps between two components that can be made more gradual or is smoothed out by the oil component/composition as it spreads and covers the two mesh devices to form a single unified device. The underlying abrupt step transition is smoothed over by the more gradual drop of the oil component/composition used to form the barrier layer 10, which is then cured to maintain the smoothing transitions 64 and 65. This optional smooth transitions 64 and 65, depending on the location of the barrier device 11' implantation, can be helpful in reducing or eliminating an edge that would otherwise fill in with connective tissue. If the anchoring support element 60 and/or reinforcing support truss structure were tack welded, or otherwise fixed, to the underlying mesh 40 and implanted in a patient without the addition of the oil component/composition that is cured to form the barrier layer, then there would be a more abrupt step transition that would exhibit a more pronounced edge. The optional smooth transitions 64 and 65 created by the provision of the barrier layer 10 in combination with the anchoring support element 60, reinforcing support truss structure 61 and the underlying mesh 40 structure creates a barrier device 11' that does not have any abrupt or sharp edges that could cause irritation when placed against tissue. Over time, the bio-absorbable barrier layer 10 is absorbed into the tissue (along with any therapeutic agent that may be provided in the barrier layer 10) and tissue in-growth occurs, replacing the barrier layer 10 and smooth transition 64 with healed tissue.

It should be additionally noted that FIG. 12 further illustrates that which has been previously described, which is the existence of a relatively thinner barrier layer 10 at a top side 66 of the barrier device 11' and a relatively thicker barrier layer 10 at a bottom side 68 of the barrier device 11'. This, again, is the result of the oil component/composition being applied to the mesh structure and sliding down (due to gravity) to pool at the bottom side 68 of the mesh 40 prior to being cured. Once cured, the barrier layer 10 maintains this structure until implanted and absorbed away over time. The thicker barrier layer 10 on the bottom side 68 of the mesh 40 can provide desired smooth side (or alternatively a rough finish) of the barrier device 11', while the top side 66 of the barrier device 11' has the thinner barrier layer 10 resulting a less smooth (i.e., irregular) finish creating the rougher side. The rougher side provides an environment more predisposed to promoting faster tissue in-growth or surface incorporation, while the smoother bottom side 68 exhibits a more delayed form of the modulated healing and is more predisposed to provide an extended adhesion-limiting functionality.

As understood by one of ordinary skill in the art, the properties of the mesh 40 and the barrier layer 10 can vary. There may be a requirement for the mesh 40 to have one side, or a portion of a side (or of the barrier layer surface), that has adhesion-limiting properties and modulated healing properties for a period of several days. Alternatively, multiple sides of the mesh 40 may be required to have extended modulating healing or extended adhesion-limiting properties. As such, the barrier layer 10 can be applied to all sides, or portions of sides, or portions of one side of the mesh 40.

In addition, the requirement may be for the adhesion-limiting properties to last several weeks, or even longer. Accordingly, the rate of bioabsorbtion can also be varied by changing such properties as amount of cross-linking, thickness, and existence of additives, such as vitamin E compounds to achieve longer or shorter term adhesion-limiting properties. In addition, there may be a desire to include a therapeutic agent to reduce inflammation, provide antibiotic therapy, or other therapeutic measures, in combination with the use of the mesh 40. Accordingly, the therapeutic agent(s) can be added to the barrier layer 10 to achieve the desired controlled release of the therapeutic agent after implantation. As previously described, combinations of cured oils top coated with lesser cured or non-cured oils and therapeutic agents can form the barrier layer 10.

The particular properties or characteristics of the mesh 40 are determined based on the desired use of the mesh 40. A common implementation is for the mesh 40 to be formed of a bio-compatible material, such as polypropylene, however other bio-compatible materials can be utilized, such as a mesh formed of the same or similar substance as the barrier layer 10 (i.e., oil based).

Example #1

An embodiment of the present invention was implemented in a rat model to demonstrate the performance of the barrier layer of the present invention relative to other known surgical mesh devices. The devices were implanted in a rat to repair abdominal wall defects. Healing characteristics, adhesion formation and tenacity, and inflammatory response associated with these materials were compared.

A polypropylene mesh material (PROLITE™) provided by Atrium Medical Corporation of Hudson, N.H., coated with one embodiment of the barrier layer described herein. The polypropylene mesh with barrier layer was compared with a bare polypropylene control mesh, and DUALMESH® biomaterial provided by W. L. Gore & Associates, Inc.

Five samples of each mesh type were implanted according to a random schedule. On the day of surgery, the animals were anesthetized with an injection of 50 mg/kg Nembutal IP. The animal was prepped for surgery, and a midline abdominal incision was made. A portion of rectus muscle and fascia was removed leaving an approximately 20 mm×30 mm full thickness defect in the abdominal wall. Using 4-0 Prolene, the appropriate patch was sutured into place repairing the existing defect. An overlap of mesh was placed over the defect to ensure proper repair, with the mesh samples being 2.5 cm×3.5 cm in size. The mesh was placed such that the smoother side was toward the viscera in the case of the polypropylene mesh with barrier layer, and the appropriate side of the Gore DUALMESH® was also placed towards the viscera. Suture knots were made on the abdominal wall side of the implant rather than the visceral side as to not interfere with tissue attachment. The mesh was sutured around the entire perimeter to ensure adequate placement. The subdermal and subcutical layers were closed with Vicryl. The skin was closed using surgical staples. The animals received Buprenorphine for pain. The mesh was explanted at approximately 30 days.

Sample Explanation:

Approximately 30 days after implantation, the animals were again anesthetized for explant of the mesh samples. The skin staples were removed, and a vertical incision through the skin and subcutaneous tissue was made lateral to both the implantation site and patch. Through this incision, the implant was inspected and photos were taken to document adhesion formation. Upon gross examination, the same investigator evaluated each sample for adherent intraperitoneal tissues and assigned an adhesion grade to each sample (Jenkins S D, Klamer T W, Parteka J J, and Condon R E. A comparison of prosthetic materials used to repair abdominal wall defects. Surgery 1983; 94:392-8). In general, the adhesions were scored as: 0-no adhesions; 1-minimal adhesions that could be freed by gentle blunt dissection; 2-moderate adhesions that could be freed by aggressive blunt dissection; 3-dense adhesion that require sharp dissection.

Once the gross evaluation was complete, the mid-portion of the abdominal cavity was excised including the implant, and adhesive tissue not completely separated from the implant, and the overlying subcutaneous and skin. Sections were then fixed and processed for histological evaluation. The histology samples were stained with Hematoxylin and Eosin, Trichrome, GS1, and Vimentin.

Results

Polypropylene Mesh Control:

These patches had a mean adhesion score of 2.1. Adhesions consisted of omentum, epididymal fat, and one had intestinal adhesions. Many of the adhesions were at the edges of the patch/tissue interface. The adhesions required aggressive blunt dissection to remove them. There was a moderate inflammatory response associated around the fibers of the mesh. There was a tight association of fat to the implant surface on the peritoneal cavity side, meaning the adhesions were not fully removed.

Gore DUALMESH® Control:

Patches were entirely covered with adhesions. The adhesions consisted of epidiymal fat, omentum and bowel. The mean adhesion score was 2.9. There was a capsule covering the entire patch that needed sharp dissection to free from material. Adhesions pulled free from capsule with blunt dissection. A moderate to severe inflammatory response was observed in association with the skin side of the implant. The thin fibrous capsule on the peritoneal side of the implant was avascular and in some implants was loosely adherent to associated tissue.

Polypropylene Mesh with Barrier Layer (Embodiment of Present Invention):

These patches had a mean adhesion score of 1.6. Adhesions included epididymal fat and some omentum. The adhesions dissociated from the patches relatively easily. There was a mild to minimal inflammatory response associated with the exposed polypropylene fibers of this material. Vimentin staining showed a layer of mesothelial cells formed on the tissue on the peritoneal cavity side of the implant.

The polypropylene mesh with barrier layer in accordance with one embodiment of the present invention showed good results in terms of adhesion minimization, tenacity of adhesions formed, and a low inflammatory response. The coated mesh product was also easy to handle, place, and suture for repair of an abdominal wall defect in this model.

Example #2

Figure 17:
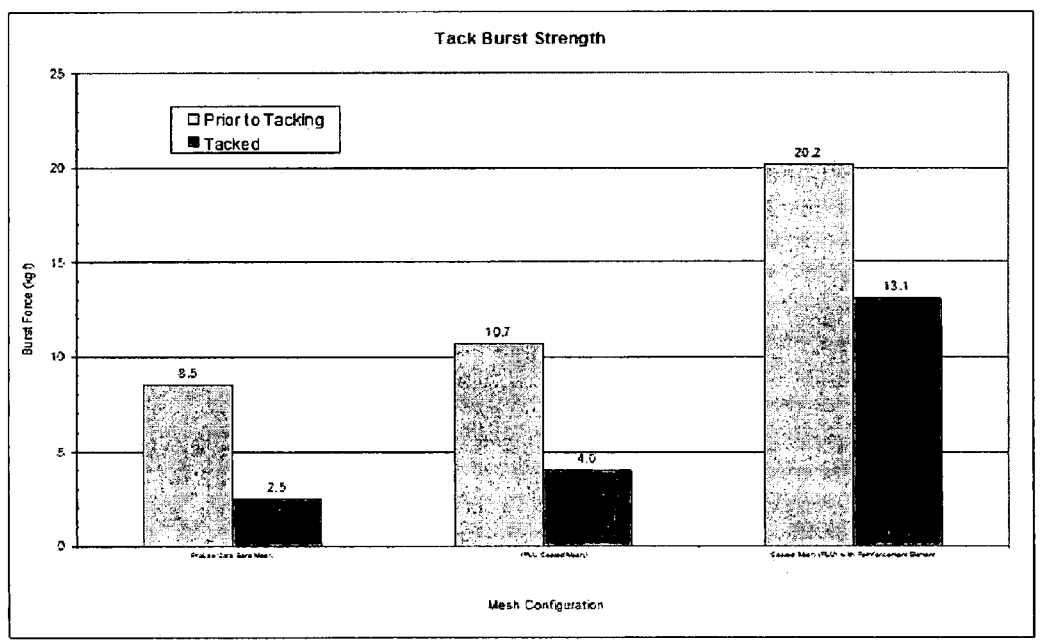
FIG. 17 is a chart of mechanical testing data regarding tack burst strength for EXAMPLE #2.

Mechanical testing has been conducted showing an increase in burst strength with the reinforcement element compared to a device without the additional reinforcement element. Testing was conducted using an Instron device to measure burst strength both with and without a 5 mm titanium tack inserted into the device. The material was hydrated in phosphate buffered saline for 1 hour at 37° C. A 1"×3" strip was laid over a piece of 0.5" thick rubber backing material, and the 5 mm ProTack™ titanium helical tack was used to fasten the mesh to the underlying rubber substrate. The test strip, with the rubber attached was laid over a cylinder with a 1.875" opening in the center that was attached to the bottom jaw of the Instron device. A ring of the same diameter was placed on top of the mesh strip and clamped in place to keep the material from moving during the test. A 0.25" diameter rod was attached to the top Instron jaw, directly above the mesh. The rod was forced through the mesh where the tack was inserted at a constant displacement rate of 300 mm/min and the burst strength of the mesh was recorded. Strips of mesh without tacking were tested in a similar manner to determine the effect of the tack on the burst strength of the material. The results are shown in the chart of FIG. 17.

These data clearly show that the inventive article significantly increases the mechanical fixation strength.

The oil component itself, in the form of fish oil for example, can provide therapeutic benefits in the form of reduced inflammation, and improved healing, if the fish oil composition is not substantially modified during the process that takes the fish oil and forms it into the barrier layer 10. Some prior attempts to use natural oils as coatings have involved mixing the oil with a solvent, or curing the oil in a manner that destroys the beneficial aspects of the oil. The solvent utilized in the example barrier layer 10 embodiment of the present invention (NMP) does not have such detrimental effects on the therapeutic properties of the fish oil. Thus, the benefits of the omega-3 fatty acids, and the EPA and DHA substances are substantially preserved in the barrier layer of the present invention.

Therefore, the barrier layer 10 of the present invention includes the bio-absorbable biocompatible oil (i.e., fish oil). The barrier layer 10 is thus able to be absorbed by the cells of the body tissue. With the present invention, because of the lipophilic action enabled by the bio-absorbable lipid based barrier layer 10 of the present invention, the intake by the tissue cells of the barrier layer 10, and any therapeutic agent component, is substantially controlled by the cells themselves. In configurations using polymer based materials, the drugs were released at a rate regardless of the reaction or need for the drug on the part of the cells receiving the drug. With the barrier layer 10 of the present invention, the cells can intake as much of the barrier layer 10, and correspondingly the therapeutic agent, as is needed by the damaged cell requiring treatment.

In addition, the bio-absorbable nature of the barrier layer 10 results in the barrier layer 10 being completely absorbed over time by the cells of the body tissue. There is no break down of the barrier layer 10 into sub parts and substances that are inflammatory and are eventually distributed throughout the body and in some instances disposed of by the body, as is the case with biodegradable synthetic polymer coatings. The bio-absorbable nature of the barrier layer 10 of the present invention results in the barrier layer 10 being absorbed, leaving only the medical device structure, if the barrier layer 10 is not implanted alone. There is no inflammatory foreign body response to the barrier layer 10.

Furthermore, the barrier layer 10 provides a lubricious and/or adhesive surface against tissue, such that the layer sticks or adheres to tissue against which it is placed. The barrier layer 10 can additionally provide an adhesion-limiting barrier between two sections of tissue, or the barrier layer 10 can form an adhesion-limiting surface on a medical device, such as the mesh 40. The use of the naturally occurring oil, such as fish oil, provides extra lubrication to the surface of the medical device, which helps to reduces injury. With less injury, there is less of an inflammatory response and less healing required. Likewise the fatty acid derived cross-linked gel that makes up the barrier layer maintains anti-inflammatory properties which also substantially lowers the inflammatory response of the tissue. The reduced inflammation also reduces adhesions.

Combination of the barrier layer 10 coating or material with the mesh 40, and in some instances the mesh 40 and anchoring support element 60, creates the barrier device 11, 11' that exhibits strong structural integrity, a resistance to tearing even when punctured, and good flexibility, while also providing an adhesion-limiting, anti-inflammatory, and/or non-inflammatory coating that is fully bio-absorbable leaving a biocompatible structure that supports tissue in-growth and encapsulation. The added strength of the anchoring support element 60 provides a swath (or additional layer) of mesh material through which the medical user can insert anchors, sutures, or tacks, or to which adhesive can be applied, to hold the barrier device 11, 11' in place until the tissue grows to envelope the device 11, 11'. The barrier layer 10 provides for a smooth transition between instances of the anchoring support element 60 and the underlying mesh 40 structure, preventing irritation from abrupt edges of material. The flexibility of the mesh 40 is likewise maintained even with the addition of the anchoring support element 60.

Figure 13:
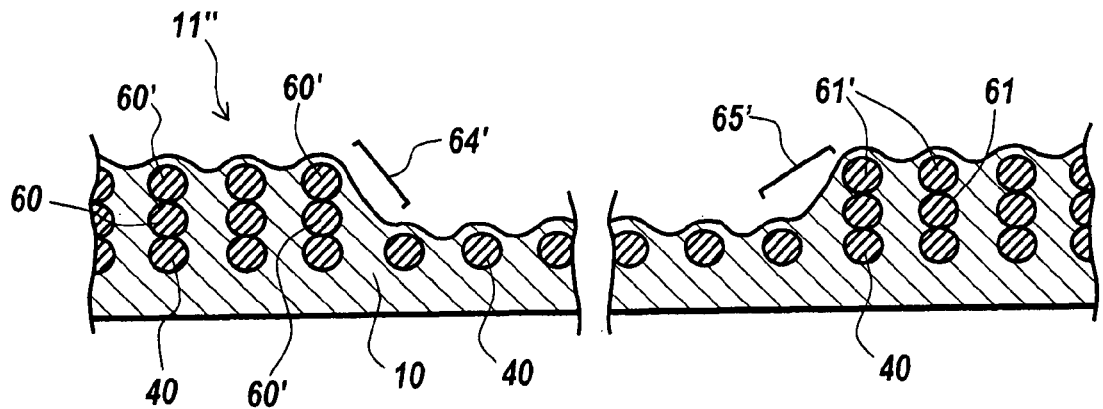
FIG. 13 is a diagrammatic illustration of a barrier device having multiple layers of anchoring support elements, in accordance with a plurality of embodiments of the present invention.

FIG. 13 is a diagrammatic illustration of yet another embodiment of a barrier device 11" in accordance with aspects of the present invention. The barrier device 11" includes the underlying mesh 40, the anchoring support element 60, and the reinforcing support truss structure 61. A second layer of anchoring support element 60' is provided on top of the first anchoring support element 60, prior to combination with the barrier layer 10. The second layer of anchoring support element 60' provides even further strengthening of the barrier device 11", increasing the resistance to tearing, and providing additional rigidity because of the increasing number of layers. A second layer of reinforcing support truss structure 61' is provided on top of the first layer of reinforcing support truss structure 61. The second layer of reinforcing support truss structure 61' provides additional strengthening of the barrier device 11" to further reduce or eliminate deformations that may occur from stress applied to the barrier device 11" during and/or after implantation. With the addition of the second layer of anchoring support element 60' and reinforcing support 61', smoothing transitions 64' and 65' require more of the barrier layer 10 to fill in the steps between the second layer of anchoring support element 60' and the underlying mesh 40 and the second layer of reinforcing support truss structure 61' and the underlying mesh 40. One of ordinary skill in the art will appreciate that a plurality of layers of anchoring support elements 60 and 60' can be coupled together and then combined with the barrier layer 10 as can reinforcing support 61 and 61'. The number of layers can vary to change strength and rigidity characteristics, and the materials used for each layer can also vary.

Figure 14A:
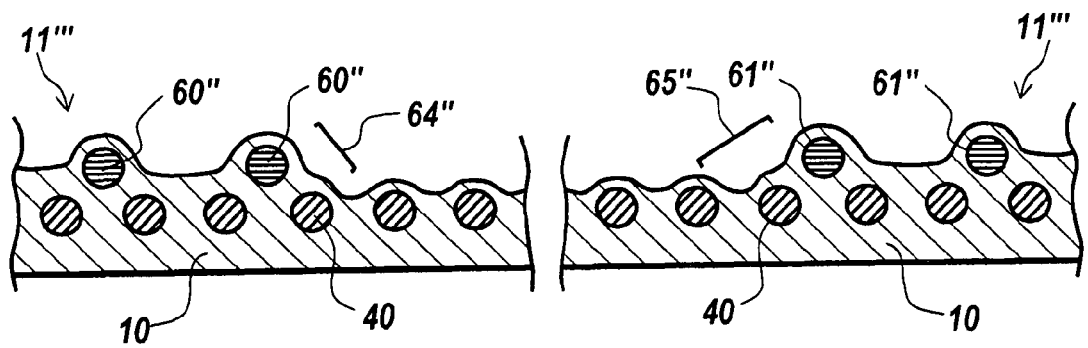
FIGS. 14A and 14B are diagrammatic illustrations of additional embodiments of barrier devices having anchoring support elements of varying structural properties, in accordance with aspects of the present invention.
Figure 14B:
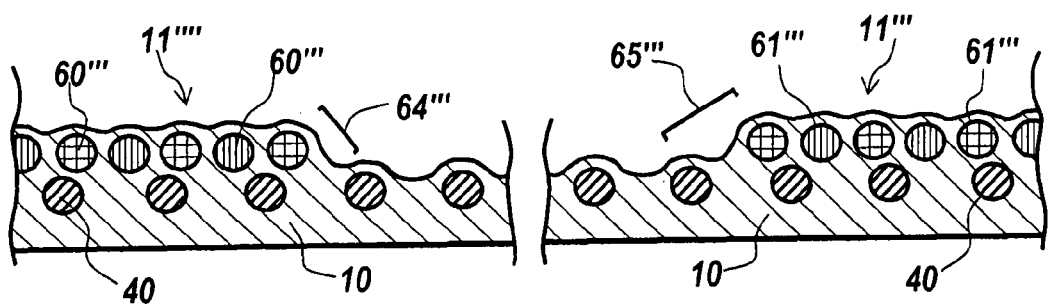

FIGS. 14A and 14B are diagrammatic illustrations of additional embodiments of a barrier device 11''', and 11'''' in accordance with further aspects of the present invention. The barrier device 11''' includes the underlying mesh 40, an anchoring support element 60", and a reinforcing support truss structure 61". The anchoring support element 60" and reinforcing support truss structure 61" provide a different mesh pattern from the underlying mesh 40. In addition, the anchoring support element 60" and reinforcing support truss structure are offset from the underlying mesh 40, meaning that the apertures between the mesh 40 elements are at least partially blocked by the anchoring support element 60" and the reinforcing support truss structure 61". Smoothing transitions 64" and 65" fill in the steps between the anchoring support element 60" and the underlying mesh 40 and the reinforcing support truss structure and the underlying mesh 40, as with other embodiments. In addition, the anchoring support element 60" and reinforcing support truss structure 61" are formed of a different material from that of the underlying mesh 40. Furthermore, in FIG. 14B, the barrier device 11'''' includes the underlying mesh 40, an anchoring support element 60''', and a reinforcing support truss structure 61'''. The anchoring support element 60''' and reinforcing support truss structure 61'''' provide still another mesh pattern from the underlying mesh 40. In addition, the anchoring support element 60''' and reinforcing support truss structure 61''' are offset from the underlying mesh 40, meaning that the apertures between the mesh 40 elements are at least partially blocked by the anchoring support element 60''' and the reinforcing support truss structure 61'''. Smoothing transitions 64''' and 65''' fill in the steps between the anchoring support element 60''' and the underlying mesh 40 and the reinforcing support truss structure and the underlying mesh 40, as with other embodiments. In addition, the anchoring support element 60''' and reinforcing support truss structure 61''' are formed of a different material from that of the underlying mesh 40. The anchor support element 60''' and reinforcing support truss structure 61''' are each formed of two different materials. The weave density of the anchoring support element 60''' and reinforcing support 61''' are also greater than that of the underlying mesh 40, while the weave density of the anchoring support element 60" and reinforcing support 61" of FIG. 14A are less dense than that of the underlying mesh 40. One of ordinary skill in the art will additionally appreciate that a variety of materials having different material properties can be used to vary the strength and rigidity characteristics of the barrier devices described herein.

Figure 15A:
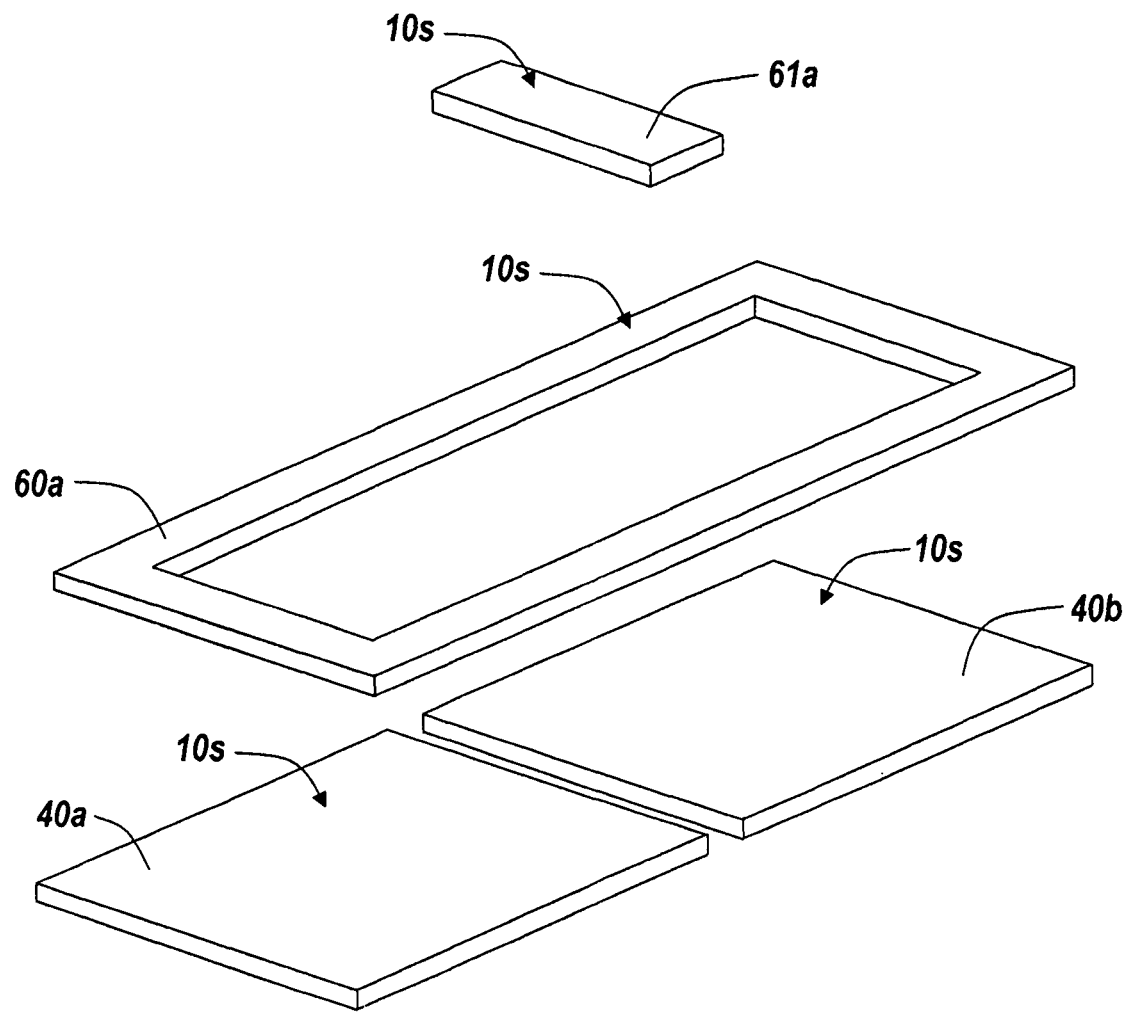
FIGS. 15A, 15B and 15C depict exemplary embodiments of a multi-piece mesh barrier device that can be implemented.
Figure 15B:
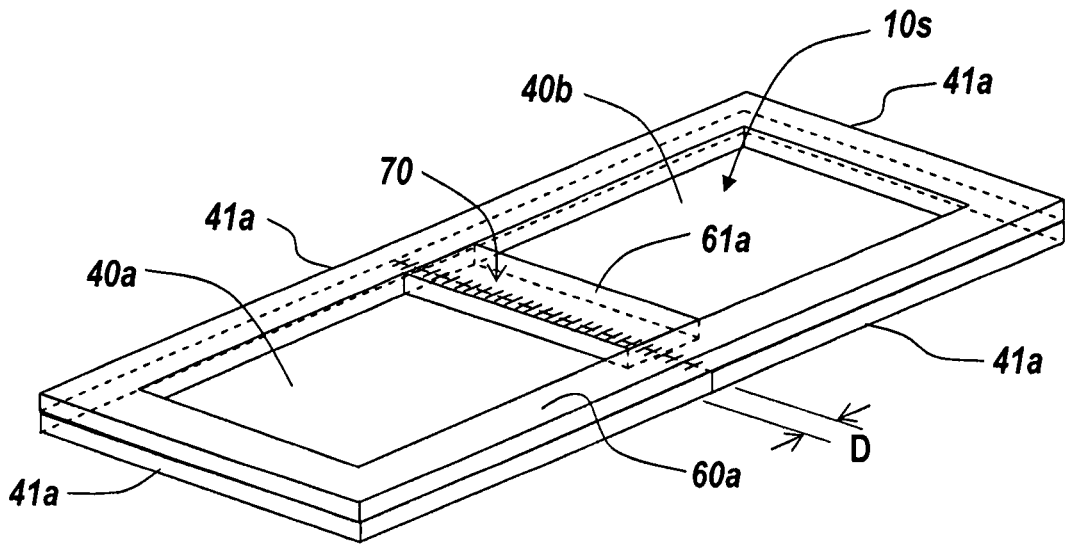
Figure 15C:
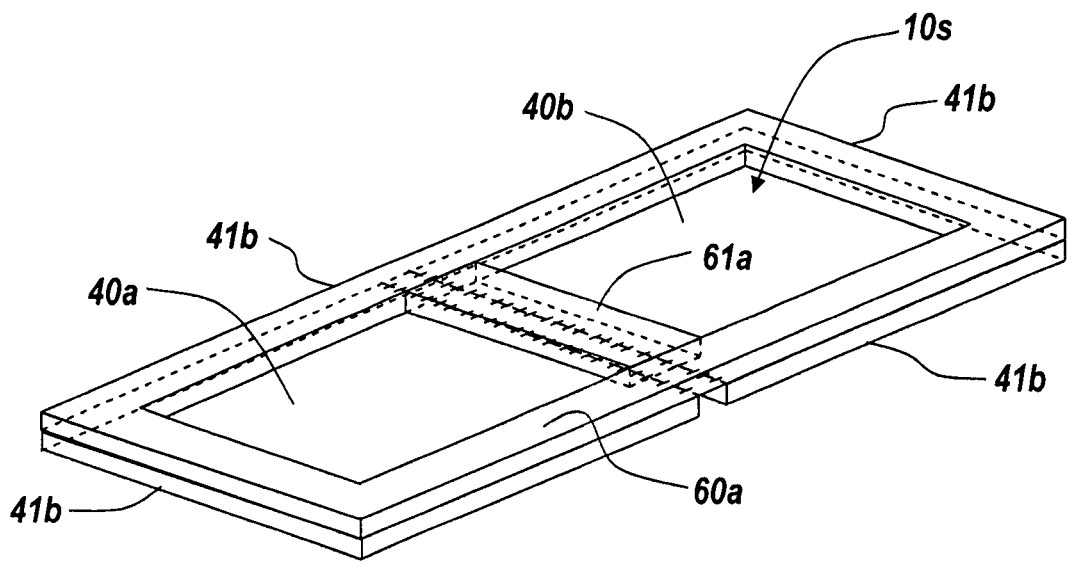

In accordance with one embodiment of the present invention, a barrier device may be implemented using a single piece of mesh or using multiple pieces of underlying mesh. Multiple pieces of mesh may be used more frequently as the size of barrier device increases due to constraints of standard loom sizes on which the mesh is formed. For example, when the size of the barrier device increases, the dimensions of the mesh required to create the barrier device may exceed the dimensions of mesh that is commonly manufactured on a loom. FIGS. 15A-C depict a reinforced barrier device 11a. FIG. 15A depicts an exploded view of the reinforced barrier device 11a. The reinforced barrier device 11a includes a first generally flexible mesh sheet 40a, a second generally flexible mesh sheet 40b, anchor support elements 60a, and reinforcing support truss structure 61a. A barrier layer, as described herein, can be added before and/or after barrier device 11a is created. The first mesh 40a has a first mesh width 84 and a first mesh length 86. The first mesh width 84 may, but is not required to be the maximum width of mesh available on a given loom of mesh. The first mesh 40a length 86 may extend to various lengths depending on the anatomical application. The second mesh 40b has a second mesh width 88 and a second mesh length 90.

A barrier layer 10s can be formed on or around the mesh 40a, the mesh 40b, the anchor support element 60a, and/or the reinforcing support truss structure prior to assemble of the barrier device 11a. The barrier layer 10s can encapsulate the mesh 40a, the mesh 40b, the anchor support element 60a, and/or the reinforcing support truss structure 61a. In some instances, as described herein, one or more tiers of the barrier layer 10s can be applied prior to assembly of a barrier device.

FIG. 15B depicts one exemplary embodiment of the assembly of the first mesh 40a, the second mesh 40b, the anchor support elements 60a, and the reinforcing support truss structure 61a to form the barrier device 11a. The first mesh 40a can be attached to the second mesh 40b using any suitable mechanism of attachment. For example, the meshes 40a and 40b can be attached by a weld, temporary or permanent adhesives, other welds (such as laser or chemical etching), or other mechanical fastening means, etc. When the first and second meshes 40a and 40b are attached they can form a seam 92. In some instances, meshes can be overlapped by a distance D when they are attached. The reinforcing support truss structure 61a is attached to the first and second meshes 40a and 40b such that the reinforcing support truss structure 61a straddles the seam 92. The reinforcing support truss structure 61a may be attached to the first and second meshes 40a and 40b using any fastening mechanisms, such as the fastening mechanisms discussed herein. Positioning the reinforcing support truss structure 61a such that it straddles the seam 92 provides reinforcement to the point or points of attachment of the first and second meshes 40a and 40b. The reinforcing support truss structure 61a can extend along the seam towards a perimeter 41a to provide additional structural support to the interior of the barrier device 11a. Further, the reinforcing support truss structure 61a also provides additional strength to the barrier device 11a itself or other portions thereof. The anchor support elements 60a can be disposed on each of the meshes 40a and 40b prior to, during or after the meshes 40a and 40b are attached using any of the fastening mechanisms discussed herein.

FIG. 15C depicts another exemplary embodiment of the assembly of the first mesh 40a, the second mesh 40b, the anchor support elements 60a, and the reinforcing support truss structure 61a to form a barrier device 11a. The first mesh 40a may be attached to the reinforcing support truss structure 61a using any suitable fastening mechanism. For example, the first mesh 40a can be attached to the support structure by a weld, temporary or permanent adhesives, or other welds (such as laser or chemical etching), etc. Likewise, the second mesh 40b can be attached to the reinforcing support truss structure using any suitable fastening mechanisms. The first and second meshes 40a and 40b may be attached to the reinforcing support truss structure 61a such that the first 40a and second meshes 40b overlap. Alternatively, first and second meshes 40a and 40b can be attached to the reinforcing support truss structure 61a such that there is no overlap between the first and second meshes 40a and 40b, as depicted in FIG. 15C. In this case, the reinforcing support truss structure 61a provides additional support to the interior of the barrier device 11a as well as to reinforce a location absent the first and second meshes 40a and 40b. The reinforcing support truss structure can straddle the area between the first and second meshes 40a and 40b and can extend towards a perimeter 41b. In some instances, the reinforcing support truss structure 61a can contact the perimeter 41b of the barrier device 11a. In other instances, the reinforcing support truss structure does not contact the perimeter 41b of the barrier device 11a. The anchor support elements 60a can be disposed on each of the meshes 40a and 40b prior to, during or after the meshes 40a and 40b are attached using any suitable fastening mechanism.

A barrier layer 10s can be formed on or around the barrier device 11a depicted in FIGS. 15B-C. The barrier layer 10s can encapsulate the barrier device 11a. In some instances, as described herein, one or more tiers of the barrier layer 10s can be applied subsequent to assembly of the barrier device 11a. Thus, the components and barrier device 11a and 11b depicted in FIGS. 15A-C can have one or more barrier layers 10s formed on or around the components and/or devices.

While the exemplary barrier device 11a assemblies in FIGS. 16A-C are depicted in a rectangular shape one skilled in the art will recognize that the barrier devices can take any shape. Further, while the FIGS. 15A-C depict a given number of meshes, anchor support elements and reinforcing support truss structures, any number of meshes, anchor support elements and reinforcing support truss structures can be used to create a barrier device in accordance with embodiments of the present invention.

Figure 16:
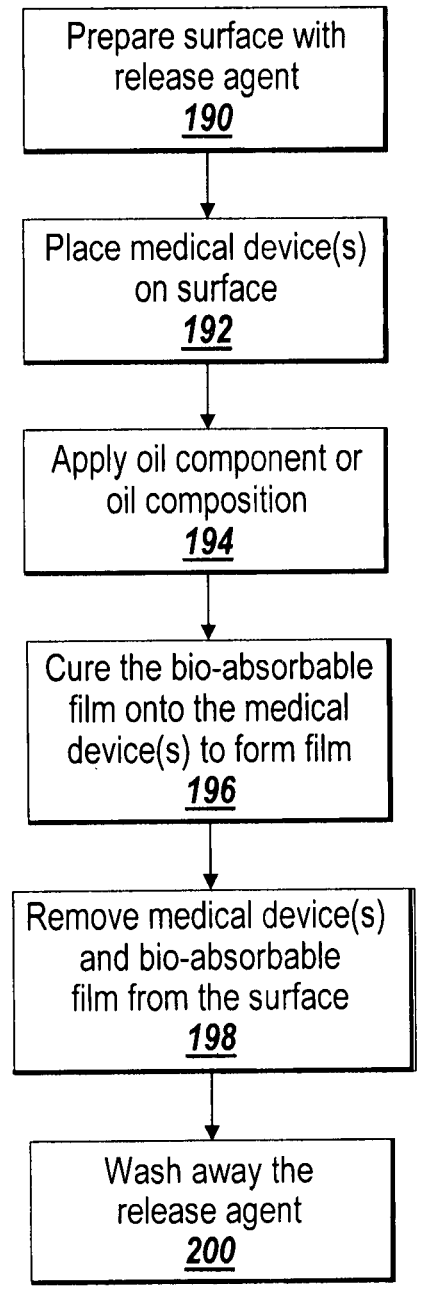
FIG. 16 is a flowchart illustrating a method of combining the barrier layer with a medical devices to form a barrier device, in accordance with one embodiment of the present invention.

FIG. 16 is a flowchart illustrating an example method of forming a barrier device in accordance with embodiments of the present invention. A surface is prepared with a release agent, such as PVA (step 190), as needed. One or more medical devices are placed on the surface (step 192). The medical devices can include one or more mesh sheet structures tack welded or otherwise fastened together with one or more anchoring support elements and/or one or more reinforcing support truss structures. It should be noted that the attachment of the anchoring support element(s) and/or the reinforcing support truss structure(s) can occur prior to the present illustrative method, as described, or can be a step in the formation of the barrier device. In addition, and as illustrated, the anchoring support element(s) and/or the reinforcing support truss structure(s) can include a plurality of elements disposed on the mesh sheet structure, if desired. The oil component or oil composition is applied to the medical device(s) (step 194). In the instance of the mesh sheet structure, the oil component or oil composition is poured or sprayed onto the mesh sheet structure. In such an embodiment the barrier layer will fall substantially to a bottom side of the mesh sheet structure (due to gravitational pull), leaving a thinner coating or amount at a top side of the mesh sheet structure, but still substantially encapsulating the mesh sheet structure within the liquid of the barrier layer material. The combined oil component/composition and the medical device(s) are then cured (step 196) using methods such as application of heat, UV light, oxygen and other reactive gases, chemical cross-linker, or hardening processes, to form the barrier layer in combination with the medical device(s). The combined barrier layer and medical device(s) are then removed from the surface (step 198) and the release agent is washed away (step 200), leaving a barrier device, such as a barrier device depicted in FIG. 9, 11A, 11B, 11C, 15B, or 15C.

As with previous methods, if desired, a therapeutic agent can be added to the oil component or oil composition at any point along the process forming the combined barrier layer 10 and mesh 40, including being a component of the oil composition. As discussed previously, consideration must be given as to whether the therapeutic agent may be affected by the curing process, or other aspects of the process.

Furthermore, the formation of the oil composition can be done in accordance with different alternatives to the methods described. For example, prior to forming the barrier layer 10, a preservative and/or compatibilizer, such as Vitamin E can be mixed with the oil component to form the oil composition. A solvent can be mixed with a therapeutic agent, and then added to the oil to form the oil composition. The solvent can be chosen from a number of different alternatives, including ethanol or N-Methyl-2-Pyrrolidone (NMP). The solvent can later be removed with vacuum or heat.

In addition, it should again be noted that the oil component or oil composition can be added multiple times to create multiple tiers in forming the barrier layer 10. If a thicker barrier layer 10 is desired, additional tiers of the oil component or oil composition can be added after steps 194 and 196. Different variations relating to when the oil is hardened or cured and when other substances are added to the oil are possible in a number of different process configurations. Accordingly, the present invention is not limited to the specific sequence illustrated. Rather, different combinations of the basic steps illustrated are anticipated by the present invention.

The barrier devices 11 of the present invention with their anchoring support elements 60 as described herein all further exhibit a feature that greatly improves visibility of the device during an implantation procedure. Specifically, through the light transmitting properties of the barrier layer 10, and specifically through the characteristics of the oil-based material that is utilized to form the barrier layer as described herein, the edges of the barrier devices 11 are illuminated when a light is applied to the barrier devices 11. Specifically, when a light is provided at various angles to illuminate an area during a surgical operation, including implantation of a barrier device 11, the light translates through the barrier layer 10 and at any cut or otherwise terminating edge, the edge is illuminated in a manner that outlines or highlights the edge relative to the other portions of the barrier device 11. This illumination of the edges of the barrier devices 11 makes it easier for a surgical user to find the edges and know where the reinforcing anchoring support elements are placed on the underlying mesh, due to the light that outlines or highlights the relevant edges.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A barrier layer device comprising:
   a generally flexible base surgical mesh sheet structure having a perimeter;
   at least one anchoring support element formed as a first additional layer of mesh material disposed on the base surgical mesh sheet structure at a location on the perimeter and configured to receive insertion of anchors therethrough when anchoring the device with anchors, wherein the at least one anchoring support element reinforces the location on the perimeter;
   at least one reinforcing support truss structure formed as a second additional layer of mesh material disposed on the base surgical mesh sheet support structure at a location not on the perimeter, wherein the support truss structure extends over less area than the base surgical mesh sheet structure, and wherein the at least one reinforcing support truss structure reinforces the location that is not on the perimeter; and
   a non-polymeric barrier layer comprising an at least partially cured and cross-linked gel, wherein the at least partially cured and cross-linked gel comprises an oil composition that includes components selected from one or more of fatty acids, glycerol and glycerides, wherein the at least partially cured and cross-linked gel includes one or more ester bonds between the components selected from fatty acids, glycerol and glycerides, and wherein the non-polymeric barrier layer is at least partially located between the base surgical mesh and each of the at least one anchoring support element and the at least one reinforcing support truss structure such that the at least one anchoring support element and the at least one reinforcing support truss structure are encapsulated in the non-polymeric barrier layer and the non-polymeric barrier layer forms a layer on a top side of the barrier layer device and a layer on a bottom side of the barrier layer device, wherein the layer on the top side is thinner than the layer on the bottom side and the layer on the top side has a rougher finish than the layer on the bottom side.

2. The device of claim 1, wherein the barrier layer is configured on two sides of the surgical mesh sheet structure.

3. The device of claim 1, wherein the barrier layer further comprises alpha tocopherol or a derivative or analog thereof.

4. A barrier layer device, comprising:
   a generally flexible base surgical mesh sheet structure having a perimeter and a pair of opposing surfaces each defined by a surface area;
   at least one anchoring support element formed as an additional layer of material disposed on either surface of the base surgical mesh sheet structure at at least one first location located near or following the perimeter and suitable for receiving insertion of anchors therethrough when anchoring the device with the anchors, the at least one anchoring support element adapted to reinforce the at least one first location, the at least one anchoring support element covering at most about sixty percent of the surface area of either surface of the base surgical mesh sheet structure;
   at least one reinforcing support truss structure disposed on either surface of the base surgical mesh sheet structure at at least one second location that is located interior to the at least one first location and different than the at least one first location, wherein the support truss structure and the anchoring support element together occupy less area than the surface area of either surface of the base surgical mesh sheet structure; and
   a non-polymeric barrier layer encapsulating at least a portion of the base surgical mesh sheet structure, the at least one anchoring support element, and the at least one reinforcing support truss structure, so as to provide a smoothing transition between the at least one anchoring support element and the portion of the base surgical mesh and a smoothing transition between the at least one reinforcing support truss structure and the portion of the base surgical mesh, wherein the smoothing transition between the at least one anchoring support element and the portion of the base surgical mesh fills in a step between the at least one anchoring support element and the portion of the base surgical mesh, and the smoothing transition between the at least one reinforcing support truss structure and the portion of the base surgical mesh fills in a step between the at least one reinforcing support truss structure and the portion of the base surgical mesh;
   wherein the barrier layer is formed of a cured, or at least partially cured, oil composition that comprises fish oil having at least one fatty acid compound, wherein the cured oil composition forms a cross-linked gel comprising one or more ester bonds between the fatty acids, glycerol and glycerides.

5. The device of claim 4, wherein at least one end of the at least one reinforcing support truss structure contacts the perimeter.

6. The device of claim 4, wherein the at least one reinforcing support truss structure does not contact the perimeter.

7. The device of claim 4, wherein the at least one reinforcing support truss structure comprises a biocompatible mesh.

8. The device of claim 4, wherein the generally flexible base surgical mesh sheet structure is comprised of a first mesh and a second mesh sheet structure coupled together forming a seam.

9. The device of claim 8, wherein the at least one reinforcing support truss structure is coupled to the first and second base surgical mesh sheet structures straddling the seam.

10. The device of claim 4, wherein the base surgical mesh sheet structure comprises a first mesh sheet structure and a second mesh sheet structure, wherein the first and second mesh sheet structures are coupled to the at least one reinforcing support truss structure.

11. The device of claim 4, wherein the barrier layer generates a modulated healing effect on injured tissue contacting the barrier layer upon implantation.

12. The device of claim 4, wherein the barrier layer comprises a physical adhesion-limiting barrier.

13. The device of claim 4, wherein the barrier layer comprises at least one therapeutic agent component.

14. The device of claim 13, wherein the therapeutic agent component comprises an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, adhesion-limiting agents, germicides, analgesics, prodrugs, and antiseptics.

15. The device of claim 4, wherein the barrier layer further comprises at least one component selected from a group of components consisting of an additional oil component, a therapeutic agent component, a solvent, and a preservative.

16. The device of claim 4, wherein the barrier layer is bio-absorbable.

17. The device of claim 4, wherein the barrier layer maintains anti-inflammatory properties.

18. The device of claim 4, further comprising at least a second reinforcing support truss structure disposed on the surface of the base surgical mesh sheet structure.

19. The device of claim 4, where the at least one reinforcing support truss structure maintains a structurally different mesh pattern from the base surgical mesh sheet structure.

20. The barrier layer device of claim 4, wherein the non-polymeric barrier layer forms a layer on a top side of the barrier layer device and a layer on a bottom side of the barrier layer device, wherein the layer on the top side is thinner than the layer on the bottom side.

21. The barrier layer device of claim 20, wherein the layer on the top side has a rougher finish than the layer on the bottom side.

22. The barrier layer device of claim 4, wherein the barrier layer further comprises a vitamin E compound.

23. The barrier layer device of claim 4, wherein the at least one anchoring support element and the at least one reinforcing support truss structure are formed of a different material from that of the base surgical mesh sheet structure.

24. The barrier device of claim 23, wherein the at least one anchoring support element and the at least one reinforcing support truss structure are offset from the base surgical mesh sheet structure.

* * * * *